United States Patent [19]
Crabtree et al.

[11] Patent Number: 5,620,887
[45] Date of Patent: Apr. 15, 1997

[54] TRANSCRIPTIONAL COFACTOR DCOH

[75] Inventors: Gerald R. Crabtree, Woodside; Dirk B. Mendel, Santa Clara, both of Calif.

[73] Assignee: The Board of Trustees fot the Leland Stanford Junior University, Palo Alto, Calif.

[21] Appl. No.: 340,136

[22] Filed: Nov. 15, 1994

Related U.S. Application Data

[62] Division of Ser. No. 156,383, Nov. 22, 1993, Pat. No. 5,403,712, which is a continuation of Ser. No. 809,436, Dec. 17, 1991.

[51] Int. Cl.$^6$ ............ C12N 15/85; C12N 15/12; C07H 21/04
[52] U.S. Cl. ............ 435/325; 435/69.1; 435/172.3; 435/320.1; 536/23.1; 536/23.5
[58] Field of Search ............ 435/6, 69.1, 172.3, 435/252.3, 320.1, 240.2; 536/23.1, 23.5; 935/77, 78

[56] References Cited

PUBLICATIONS

G. Courtois, et al. (1987) Science: 238:688–692. Interaction of a Liver–Specific Nuclear Factor with the Fibrinogen and α–antitrypsin Promoters.
H. Maguire, et al. (1991) Science 252:842–844. HBV X Protein Alters the DNA Binding Specificity of CREB and ATF–2 by Protein–protein Interaction.
K. Ullman, et al. (1991) Science 254:558–562. Activation of Early Gene Expression in T Lymphocytes by OCT–1 and an Inducible Protein OAP$^{40}$.
B. Lewin 91990) Cell 61:1161–1164. Commitment and Activation at Pol II Promoters: A Tail of Protein–protein Interactions.
S. Stern, et al. 91989) Nature 341:624–630. The Oct–1 Homeodomain Directs Formation of a Multiprotein–DNA Complex with the HSV Transactivator VP16.
K. Stringer, et al. (1990) Nature 345:783–786. Direct and Selective Binding of an Acidic Transcriptional Activation Domain to the TATA–ox Factor TFIID.
Y. Lin and M. Green (1991) Cell 64:971–981. Mechanism of Action of an Acidic Transcriptional Activator in Vitro.
S. Berger, et al. (1990) Cell 61:1199–1208. Selective Inhibition of Activated But Not Basal Transcription by the Acidic Activation Domain of VP16: Evidence for Transcriptional Adaptors.

R. Kelleher et al. (1990) Cell 61:1209–1215. A Novel Mediator Between Activator Proteins and the RNA Polymerase II Transcription Apparatus.
B. Pugh and R. Tjian (1990) Cell 61:118701197. Mechanism of Transcriptional Activation by SP1:Evidence for Cofactors.
P. Flanagan, et al. 91991) Nature 350:436–438. A Mediator Required for Activation of RNA Polymerase II Transcription in Vitro.
G. Courtois, et al. (1988) P.N.A.S. 85:7937–7941. Purified Hepatocyte Nuclear Factor 1 Interacts with a Family of Hepatocyte Specific Promoters.
S. Cereghini, et al. 91990) EMBO J. 9:2257–2263. Hepatocyte Dedifferentiation and Extinciton is accompaniedby a Block in the Synthesis of mRNA Coding for the Transcription Factor HNF1/LFB1.
C. Kuo, et al. (1991) EMBO J. 10:2231–2236. Independent Regulation of HNF–1α and HNF–1β by Retinoic Acid in F9 Teratocarcinoma Cells.
D. Mendel and G. Crabtree (1991) J.B.C. 266:677–680. HNF–1, a Member of a Novel Class of Dimerizing Homeodomain Proteins.
D. Mendel, et al. (1991) Genes and Development 5:1042–1056. HNF–1α and HNF–1β(HNF–1) Share Dimerization and Homeo Domains, but not Activation Domains, and Form Heterodimers in Vitro.
J. Kadnaga and R. Tijan (1986) P.N.A.S. 83:5889–5893. Affinity Purification of Sequence–specific DNA Binding Proteins.
S. Baumhueter, et al. (1990) Genes & Development 4:372–379. HFN–1 Shares Three Sequence Motifs with the PUO Domain Proteins and is Identical to LF–B1 and APF.

*Primary Examiner*—John LeGuyader
*Assistant Examiner*—Sean McGarry
*Attorney, Agent, or Firm*—Pamela J. Sherwood; Fish & Richardson P.C.

[57] ABSTRACT

Methods and compositions are provided for producing and utilizing nucleic acid and peptide sequences associated with cofactors which bind to transcription factors to enhance transcriptional activity of the transcriptional factors and maintain the transcriptional factors as dimers. The compositions can be used for modulating expression of genes, particularly coordinately regulated genes, as evidenced by the combination of the transcription factors HNF-1α and -1β with the cofactor DCoH.

7 Claims, 9 Drawing Sheets

```
rat      1  GAATTCCGGTTTTATAGCAAGGACATTACATTTTCAGGTACCTAAAGTCAAAATTCAACA human
mouse
rat    121  AGTAACATTTACAAAAAGAGGCAGAGGCAGGGGGATCTCTGCCCCGCCCCCGCGGTGGCC
DCoH     1 human        -----A---------------C---------GA-----------A-------------A-----
mouse        ------------C--C-----G--A-----------------------A-----
rat    241  GGCAAGGCACACAGGCTGAGTGCTGAGGAACGGGACCAGCTGCTGCCAAACCTGCGGGCT
DCoH     3   G  K  A  H  R  L  S  A  E  E  R  D  Q  L  L  P  N  L  R  A human        ------------C-----G----------------G--------------G--A---------
mouse        ---------------------------------A------------------------
rat    361  TTCAACAGGGCTTTTGGCTTCATGACAAGAGTCGCCCTGCAGGCTGAAAAGCTGGACCAC
DCoH    43   F  N  R  A  F  G  F  M  T  R  V  A  L  Q  A  E  K  L  D  H human        -----C------A---------C------------------------------A--C-----C
mouse        ----------G-----------------------------------------C---------
rat    481  GCCGGTCTTTCTGAACGGGATATAAACCTGGCCAGCTTCATCGAACAAGTTGCCGTGTCT
DCoH    83   A  G  L  S  E  R  D  I  N  L  A  S  F  I  E  Q  V  A  V  S human        GGAGTCCAGGGAGGGAGCTGAGGAGCCCTTACCCTCCCACCACTCCCCTCCCAAGACCCA
mouse        CTAGGAAGGGAACCAAGGAGGCTGGCCCTTGCTCCCTGACTCTTTCAGTGACCACCACCT
rat    601  GAGGAACCCAGGGAGGGAACCAAGGAGGCTGGCCCTTGCTCCCTGACTCTTGCGGTGACC human        AGGAATTTAGACCTTTTCCCTGCACCACTCTCTTCATCCTGGGGGGCTCTGTTACACTAA
mouse        CTCCTCACTGGGGCTCTGCCATGTTACACTAATTTGAATAAGCTCTCCCTTTTTCTGTAG
rat    721  GTGCCAGCCTCCTCACTGGGCTCTGCCATGTTTATAATTTGAATAAGCTCTCCCATTTTC human        GGCCGTCTCTTGCTCCCTAATTCATTTCCCAGGAAGCTGTGATACAGGGTGAAATAAAGT
mouse        TCATTTTCCAAGGTAGCTGTGATAAAGCATGACATAAAAGCCCAATTCAGATCCTACTAA
rat    841  TAGTTAATTTTCCAAGTAGCTGTGATAAAGCATGACAGAAAGTCCAATTCAGACCCTACT human        ATGTCTCAAATAAAACTATTATATCACTTGGTAAAAAAAAAAAAAAAAAAGAATTC
mouse        TATCGATGAAAAAAAAAAAAAAAAGGAATTC
```

FIG. 1C-1

```
CACTGATATAAAACTTCTATTTAAACCAATAGGGTTCTGTTATGATATTGATCTGTTCAC   120

TGCTGCCTGCCAGCCGCTCTCCCTCGCTGACGCCACCTGCTTCCCGCACTGGACATGGCT   240
                                                        M  A
                                                           2

-----------------G-----------T---------------G-----T-----C------
-----------------G-A------------T---------G----------------------
GTGGGGTGGAATGAACTGGAAGGCCGAGATGCCATCTTCAAACAGTTCCATTTTAAAGAC   360
V  G  W  N  E  L  E  G  R  D  A  I  F  K  Q  F  H  F  K  D    42
      (mouse) V -----T--A---------------------C-----GC-----------T--G---
---------------------------------------------------T------
CATCCCGAGTGGTTTAACGTGTACAACAAGGTCCATATCACCTTGAGCACCCACGAATGT   480
H  P  E  W  F  N  V  Y  N  K  V  H  I  T  L  S  T  H  E  C    82

------TAGACCCTGCCCTTCCTTCTTTGAATTCTTCCGGGGGAAAGGGTGACTGAACTG
------TAGATCTACCCTGACTCTTATTTGCTTGGGGGAAGGAGTGACTGGAGGAGGAAC
ATGACATAGATCTACCCTGCCTCCTATTTCCTTAGGGGAAAGGAGAAGGAGTGACTGGAG   600
M  T  *                                                       104

GCCGCCGCCGTTGAGGGCTGAGTCCTTGCTGTGGGATGTGCCAGTGTCCCCACCAACACC
CCCTATGCAGAAGGGATGTCAATGTCAACAGCAGGGACTGAGACCTTTCTCTGTGCCACT
ACCATCTCCGTCAGGAGGGGTATGAGTCCCTCCCTGTGCAGAACGATGCCCATGTTCCTG   720
TGTAATAAACTCTCCCCTTTTCTTTGCAACTTCCCAGCAACAATAATGATTTTCTTGCCA
AGTTCCCAGCCTCAGTAATGTTCCAGGCTGGCTTCTTGTTCCTTTTCTACCCTTTCTAGT
TATAGAGTTCCTAGCCTCAGTTGTGTCCCAGGCTGCCTCTTGCTCCTTGTCTACCGGTTC   840
CTTGTCTTAGAAACCAGGACCCTAAACCCCACACTATGTAATAGAAACACATGTGTTTTT
TAAAACAAGCTCCAATGTATTATGGAAACATGTGCTTTTACGCCTCCAATAAAACTATGT
AAAACAAACCCCAATATATTATGGAAACAGTGCTTTTATGCCGGAATTC             949
```

FIG. 1C-2

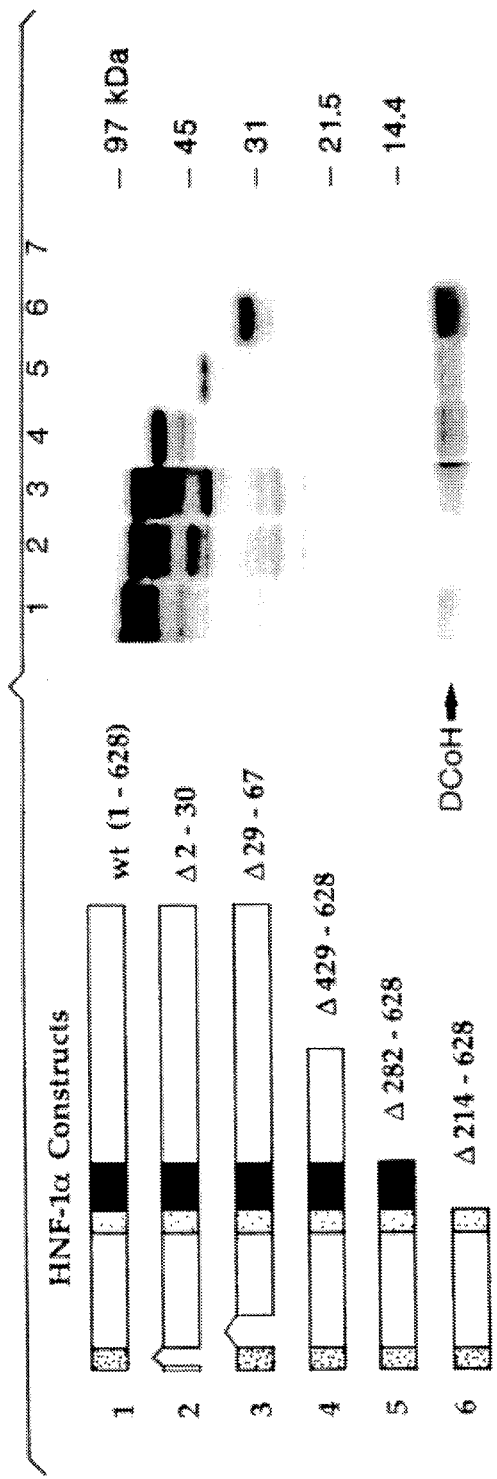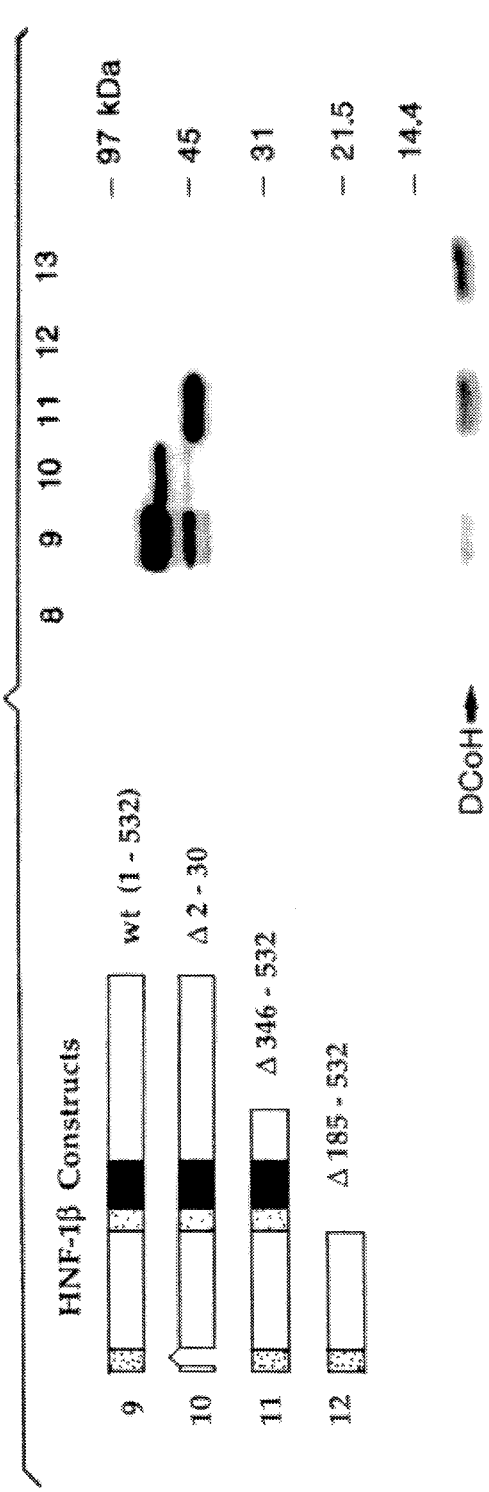
FIG. 2A
FIG. 2B 208 nt ▶

227 nt ▶

TRANSCRIPTIONAL COFACTOR DCOH

The research carried out described in the subject application was supported at least in part by grants HL33942, HD07201 and GM07149 from the National Institutes of Health. The government may have rights in any patent issuing on this application.

CROSS REFERENCE TO RELATED APPLICATIONS

This application is a division of application Ser. No. 08/156,383, filed Nov. 22, 1993, now U.S. Pat. No. 5,403,712, which was a continuation of application Ser. No. 07/809,436, filed Dec. 17, 1992, now abandoned.

INTRODUCTION

1. Technical Field

The field of this invention is transcriptional regulation employing transcription factors.

2. Background

The regulation of proliferation and differentiation of cells is predicated upon the ability of the cell to govern which genes are going to be expressed in an organized pattern. It has long been known that there are a number of transcriptional factors which are associated with RNA polymerase. These factors are necessary for the initiation of transcription. For the most part, these factors bind to specific DNA sequences present in the chromosome or extrachromosomal gene. Frequently, there are a plurality of the same or different transcriptional factor binding sequences, so as to result in a particular pattern of binding of the transcription factors. These transcription factors usually involve contact with other transcriptional factors, either adjacent or nonadjacent. By having varied DNA binding sequences for the factors, regulation of the genes is achievable.

In light of the extraordinary number of genes in the human chromosome, estimated to be over 100,000, the number of known transcriptional factors is insufficient to provide the desired regulation. The possibility of having a much larger number of transcriptional factors is not a particularly attractive scenario. Therefore, there has been continuous interest in being able to understand how transcription is regulated in accordance with the nature of the cell, its level of maturation, and the process of meiosis and mitosis.

By understanding the regulation of transcription, the mechanisms may be manipulated in a variety of ways for modulating expression, either up- or down-regulation, of genes of interest. In this way, one may provide for the external control of expression, inducible control under certain conditions in vivo, and the like.

Relevant Literature

For a general discussion of interaction of transcription factors, see Lewin (1990) *Cell* 61, 1161–1164. Stern et al. (1989) *Nature* 341, 624–630; Stringer et al. (1990) *Nature* 345, 783–786; and Lin and Green (1991) *Cell* 64, 971–981 describe the interaction of the protein VP-16 of herpes simplex virus with Oct-1, TFIID and TFIIB, respectively. See also, Ullman et al. (1991) *Science* 254, 558–562. Maguire et al. (1991) *Science* 252, 842–844 describe the pX protein of HPV binding to CREB and ATF-2 to change the sequence specificity of binding to CRE-like elements. Berger et al. (1990) *Cell* 61, 1199–1208; Kelleher et al. (1990) *Cell* 61, 1209–1215; Pugh and Tijan (1990) *Cell* 61, 1187–1197; and Flanagan et al. (1991) *Nature* 350, 436–438 all describe cofactors involved with the facilitation of the interaction of general transcription factors with upstream specific transcription factors.

Information concerning the transcription factors HNF-1α and -1β, which have homeodomains, may be found in Courtois et al. (1988) *Proc. Natl. Acad. Sci. USA* 85, 7937–7941; Courtois et al. (1987) *Science* 238, 688–692; Cereghini et al. (1990) *EMBO Journal* 9(7), 2257–2263; Kuo et al. (1991) *EMBO Journal* 10(8), 2231–2236; Mendel and Crabtree (1991) *J. Biol. Chem.* 266, 680; and Mendel et al. (1991) *Genes Dev.* 5, 1042–1056. Purification procedures are described in Kadonaga and Tijan (1986) *Proc. Natl. Acad. Sci. USA* 83, 5889–5893; Courtois et al. (1988) supra; and Baumhueter et al. (1990) *Genes Dev.* 4, 372–379.

SUMMARY OF THE INVENTION

Transcription of genes is modulated by controlling the interaction between transcriptional cofactors and transcription factors. The transcriptional cofactors are characterized by having a lipophilic region, being dimeric in solution, and being capable of enhancing intermolecular interaction between transcription factors. By controlling the level of the cofactors in the nucleus of a cell or by modifying the interaction between the cofactor and the transcription factor, expression of genes, particularly coordinated expression of genes, may be regulated. Compositions are provided for the regulation of transcription associated with such cofactors for gene therapy, regulation of differentiation, identification of genes having coordinated expression, improvements in the production of proteins in culture and in vivo, as well as other useful purposes.

BRIEF DESCRIPTION OF THE DRAWINGS

FIG. 1c (parts 1 and 2) are the nucleotide sequences of the transcription DCoH cofactor from different species(rat, SEQ ID NO:01human, SEQ ID NO:02, mouse, SEQ ID NO:03; DCoH, SEQ ID NO:04);

FIG. 2 (parts A and B) diagrams deletion constructs of HNF-1α and -1β and visualized SDS-PAGE gels of immunoprecipitated HNF-1α and -1β constructs and associated proteins;

DESCRIPTION OF SPECIFIC EMBODIMENTS

Figure 1B:
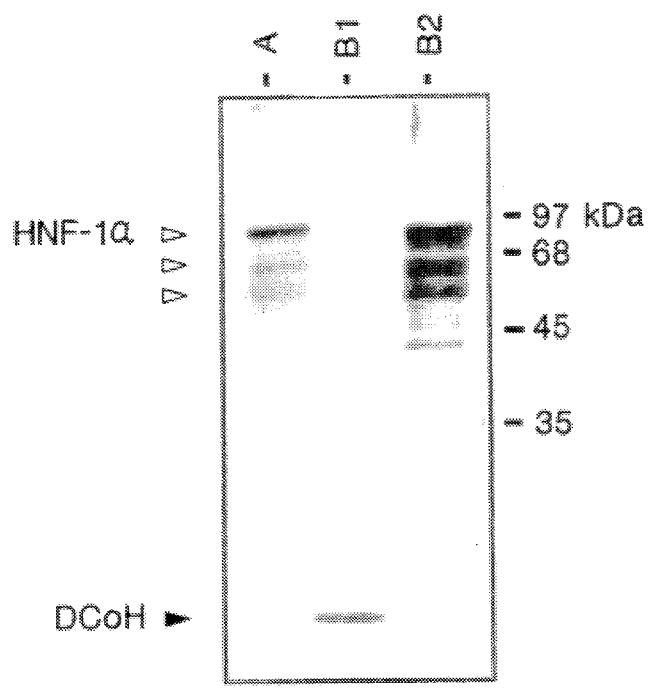
FIG. 1b is a visualized SDS-PAGE gel of the proteins eluted from the DNA affinity column.

Methods and compositions are provided relating to transcriptional cofactors ("DCoH") which are characterized by being relatively small peptides, generally under about 50 kd; having a domain of at least 20 amino acids and not more than about 50 amino acids, which is lipophilic, as characterized by having a plurality of hydrophobic aliphatic and aromatic amino acids free of side chain heteroatoms (particularly F, I, L and V); normally existing as dimers in solution; being conserved across mammalian species; being capable of enhancing dimerization of dimeric transcription factors; and having a pattern of expression among mammalian cells. Thus, the subject factors are associated with regulated transcription associated with the nature of the cell and its level of maturation.

Depending upon the purpose of the composition, it may be a naturally occurring protein, a mutated protein, a fragment thereof, a nucleic acid, either naturally occurring or synthetic, or such compounds fused to other compounds, which compoundsare associated with the purpose of the composition.

For the most part, the proteins of this invention will be under 50 kd in molecular weight, more usually under about 25 kd, and at least 5 kd, generally ranging from about 5 to 25 kd in molecular weight. These compounds may be fragmented to fragments of not less than about 8 amino acids, usually not less than about 12 amino acids, preferably at least about 18 amino acids, and generally fewer than about 100 amino acids, frequently fewer than about 60 amino acids. The fragments or the entire protein may be fused to another protein or peptide, generally of from about 200 Da to 1 MDa. Of particular interest are fragments associated with a functional domain, such as the binding domain for the DCoH with a transcription factor or with each other. Also of interest are nucleic acids encoding the peptides of this invention, which sequences may be derived from natural sequences or synthetic sequences. For the most part, the encoding nucleic acid sequences will be under about 1.5 kbp, more usually under about 3 kbp, and usually at least about 24 bp, more frequently at least about 36 bp.

These various compounds having binding specificity may be joined to a wide variety of other sequences or molecules for a variety of purposes. The molecules may be joined to other molecules to enhance stability when used in culture or in vivo, to ease transport across membranes, to direct the compound to a particular site or cell type, for ease of administration, or to modulate the binding characteristics.

Of particular interest in this family of compounds is a binding domain, which binds to the transcription factor. The binding domain will generally be of from about 20 to 50 amino acids, usually 20 to 35 amino acids, and will be characterized by being lipophilic and having a high proportion of lipophilic amino acids, both aliphatic and aromatic, particularly phenylalanine (F), isoleucine (I), leucine (L) and valine (V). Particularly, the lipophilic amino acids will be at least 10% of the amino acids, frequently at least about 15% and generally not more than about 50%, more usually not more than about 40%. In addition, the number of charged amino acids (aspartate (D), glutamate (E), lysine (K), and arginine (R)) will be not more than 50%, usually not more than about 40%, generally not more than about 35% of the sequence.

There are a large number of transcription factors binding to specific DNA sequences which are present as dimers. These transcription factors include HNF-1α and -1β, c-Jun, Jun B, Jun D, c-fos, fra, MyoD, El2, CREB, LAP, DBP, ets 1, ets 2, and others. Associated with these transcription factors will be the subject cofactors, which do not bind to the DNA associated with the transcription factors, but rather bind to the transcription factors to substantially enhance the stability of the dimer. Usually, the stability of the dimer will be enhanced at least five-fold, more usually at least ten-fold, and may be enhanced 50-fold or more, under natural binding conditions in nuclear extract. The subject cofactors will readily dimerize in solution having a substantial affinity for each other, independent of their binding to the transcription factor. The ability of the cofactors to dimerize is associated with their ability to enhance the dimeric stability of the transcription factors. The cofactors can act as "regulons" in providing for the coordinated regulation of coordinately regulated genes. Thus, by providing for controlled expression of the cofactor, where the concentration of cofactor is a limiting element in the expression of the genes, one may regulate the expression of such genes. Various genes are known to be coordinately regulated. These genes include those characteristic of the differentiated state, those coordinately induced in response to environmental stimuli and those coordinately induced in response to cytokines, hormones and other naturally occurring molecules.

Regulation can be achieved in a number of ways: (1) employing homologous recombination to change the regulatory nature of the promoter region of the cofactor; (2) introduction of antisense sequences or an antisense gene which are transcribed into a cell; (3) introduction of a ribozyme or ribozyme gene which is expressed to diminish the amount of functional messenger RNA; (4) "knocking out" the cofactor by homologous recombination; (5) introducing into the cell mimetic compounds, e.g. peptides, which can compete with the binding of the cofactor to the transcription factor or one cofactor to the other cofactor; (6) providing a gene which expresses the cofactor domain to provide for covalently bound fused cofactor; and (7) introduction of modified versions of the cofactor to enhance or diminish, or alter specificity of the coordinated interactions among transcription factors.

For modifying by homologous recombination, various techniques are available for identifying cells which have been modified at the target 1 locus. See, for example, Thomas and Capecchi, *Cell.* (1987) 51:503–512. The modifications may include replacing the transcriptional initiation region with an inducible or constitutive transcriptional initiation regulatory region, so as to change the basis upon which the cofactor is expressed. One may use homologous recombination to introduce into or remove a mutation from a particular sequence, where the mutation may result in a disease; where one may wish to change one or both of the binding regions of the cofactor to enhance or diminish the binding affinity of the cofactor in a homo- or heterodimer or with one or more transcription factors. Alternatively, one may provide for the introduction of a gene transcribing an antisense sequence where the antisense gene is under transcriptional initiation regulation which allows for constitutive production, so as to at least partially inhibit expression of the cofactor or inducible expression, which allows for the controlled variation in expression of the cofactor. Similarly, instead of an antisense gene one may provide for a ribozyme gene, where the ribozyme provides for the destruction of or truncating of the messenger RNA. By having dual control of the regulation of the expression of cofactor, one can provide for variations in response of cells to various external stimuli.

Alternatively, one may administer to the cells, either in culture or in vivo, molecules which will be transported across the membrane of the cell to act in the nucleus. For transport across a cell membrane, one may use various techniques, such as liposomes, where the liposomes are targeted to a surface membrane protein which results in endocytosis. One may use fused peptides where the peptides are fused to a sequence which is capable of passing through the membrane or binding to a surface membrane protein which results in transport of the peptide into the cell. For localization to the nucleus one may use nuclear localization sequences such as those defined for the glucocorticoid receptor or SV-40 large T antigen.

For nucleic acids, one may use various synthetic nucleic acids, which have different polymeric backbones, so as to be less susceptible to degradation, where the modifications may include the replacement of oxygen with a group less susceptible to hydrolysis, such as sulfur, methylene, or the like, or replacement of the polar oxygen with sulfur or methyl, etc. By linking the nucleic acid or peptide to a hydrophobic group, the active portion of the molecule may be transported into the cell.

The cofactors may be identified in a variety of ways. One method would be to screen a library with the entire sequence of the cofactor which binds to HNF-1α and -1β, the HNF-1 cofactor. One would use mild to low stringency, generally at a temperature less than about 50° C. and at an ionic strength equivalent to less than about 4× SSC, usually at or about 2× SSC. Other mild stringency conditions can be envisioned which are equivalent to this standard. Thus, by screening various cDNA libraries, one may detect sequences which hybridize with the HNF-1 cofactor. In accordance with conventional ways, one may then sequence the clone and establish the presence of a full sequence for expression.

Various techniques may be employed for identifying the factor with which the cofactor binds. One may express the identified cofactor, prepare monoclonal antibodies to such cofactor, and then use such monoclonal antibodies with a lysate of cells from which the library was prepared. A complex of the cofactor and its transcription factor should be capable of isolation. The transcription factor may then be identified by fragmenting and determining one or more sequences and comparing these sequences to known transcription factors. Where no sequence can be found to have homology, one may then sequence the entire transcription factor to identify a new transcription factor. Where homology is found with a known transcription factor, one will then have identified the transcription factor with which the cofactor binds. Alternatively, one may add an excess of tagged identified cofactor to a lysate from which the cDNA library was obtained and by various separation techniques, e.g. electrophoresis or density gradient centrifugation, identify the complex of the cofactor with a transcription factor(s) with which it binds.

For identifying cofactors which do not have homology, one prepares nuclei or extracts in the substantial absence of detergent. One may then significantly concentrate the amount of transcription factor, by passing the resulting extract through a DNA affinity chromatography column, where transcription factors will be highly enriched. Following the enrichment, one may the use reversed phase HPLC to further enrich for the transcription factor-cofactor complex. For example, one may use a C8 reversed phase HPLC using an acetonitrile gradient for elution. The fractions which come off the column may then be further analyzed by separation techniques, e.g. gel electrophoresis under denaturing conditions, where the transcription factors and the cofactors will be separated. Alternatively, prior to loading the purified transcription factors onto the reversed phase HPLC, one may denature the proteins and pyridinylate them and obtain separation as individual molecules on the column. One may then further purify, for example, by gel electrophoresis, and then analyze in a variety of ways, using enzymatic degradation to define fragments, sequencing, and the like. Once one has identified the cofactor peptide, one may determine a sequence of the cofactor which allows for the preparation of degenerate probes and use the probes to identify cDNA or genomic fragments expressing the subject cofactor.

Alternatively, one may screen an expression library, e.g. a cDNA library where the cDNA will usually be fused to another sequence, e.g. β-gal. One could combine the expression products, in an appropriately buffered medium, e.g. pH 6–9, at low ionic strength, with a known transcriptional factor, particularly in the substantial absence of detergent. One may prepare an affinity column with the transcription factor and pass a lysate or supernatant from the expression host through the column.

One can then elute the proteins bound to the column and characterize them. Alternatively, one could combine the transcription factor with the lysate or supernatant from the expression host and identify complexes by using magnetic beads as labels for the factor, or fluorescent, radioisotopic or other label bound to the transcription factor or anti-(transcription factor) antibody for identification and isolation in accordance with known techniques. The complexing may occur in the presence or absence of DNA to which the transcription factor binds.

Of particular interest is the cofactor binding to HNF-1α and -1β, and fragments thereof and DNA sequence encoding such cofactors and fragments thereof. The HNF-1α transcription factor has a dimerization domain at the N-terminus of about 32 amino acids followed by a region of about 100 amino acids conserved between HNF-1α and -1β. These compositions may be used in a variety of ways. As already indicated, the DNA sequences may be used as probes for detection of other cofactors having homology to the subject cofactors. Sequences having as little as 30% homology, preferably at least about 50% homology, over a sequence of at least 12 bases, more usually over a sequence of at least 20 bases and more usually over a sequence of at least 30 bases, may be detected as part of a family of cofactors. The peptides may be used in affinity columns.

For the HNF-1 cofactor, a region of interest is the N-terminal region, particularly a region of about 50 amino acids, more particularly a region of about 35 amino acids from about amino acid 25 to 75, more usually 30 to 65 of the sequence, particularly having at least 20 amino acids in that sequence. In any sequence, desirably at least about 20%, more usually at least about 30% of the amino acids are lipophilic amino acids and fewer than about 40% are charged amino acids.

The proteins may be used to prepare antibodies, which may then be used for the detection of cofactors having epitopes which are cross-reactive with the subject cofactors. In this manner, lysates may be screened for the presence of cofactors. In addition, the antibodies can be used for monitoring variations in development of cells as the cells go through various phases, where the cells have been synchronized to be in the same phase; or following maturation and differentiation of the cells as associated with the particular cofactor. The cofactors with the transcription factors may be used to identify regulatory regions to which the cofactors bind, so as to identify those genes which are coordinately regulated.

The subject compositions may be used in a variety of other ways. The subject compositions may be used for screening to determine the existence of alleles, where such alleles may result in hereditary diseases. To inhibit the functioning of cofactors, one may use a dominant negative approach, where one provides for the random integration of a sequence which encodes a protein, which results in a non-functional heterodimer cofactor. In this way, one may block the expression of certain genes, where such expression is undesirable. Alternatively, one may use the genes to construct cells for the production of various proteins of interest, in vitro or in vivo. Thus, for growing cells in culture for the production of proteins of interest, particularly mammalian proteins in mammalian cells, expression of the cofactors can be used for regulation of the expression of the mammalian proteins. Particularly, where the protein of interest may interfere with the proliferation of the cells, one may provide for inducible expression of the cofactor, so that the cells may grow to the desired density, before producing the product. Alternatively, one may introduce a cofactor into embryonic cells, where the cofactor will have a regulatory region which allows for expression of the cofactor in cells in which it is not normally expressed. In this way, one may provide for expression of genes in a particular organ or site of a host where the expression products are not normally produced. By having indirect regulation of one or more genes present in the cell, one can more rapidly turn off or turn on a plurality of genes, one can use the cells natural machinery to achieve the desired results, and one may provide for greater variation in the temporal or maturational expression of genes.

The following examples are offered by way of illustration and not by way of limitation.

EXPERIMENTAL

Purification and Cloning of HNF

HNF-1α was purified from rat liver nuclear extracts by DNA-affinity chromatography (Rosenfeld and Kelly, 1986; Kadonaga and Tijan, 1986) essentially as previously described using the HNF-1 binding site of the β fibrinogen chain promoter (Courtois et al., 1988). Lauryl dimethylamine oxide (LDAO) (Calbiochem) was added to the purified HNF-1α to a final concentration of 0.03% after elution from the DNA affinity column to reduce losses of the purified protein. The purified protein, either in its native state or after being denatured (8M guanidine HCl, 10 mM DTT for 1 hr at 37° C.) and pyridinilated (20 mM 4-vinylpyridine for 15 min at 37° C.), was subsequently applied to a C8 reverse phase HPLC column (2.1×30 mm, Applied Biosystems) pre-equilibrated with 0.1% trifluoroacetic acid (TFA). Bound proteins, monitored at 214 nm, were resolved with a linear gradient of acetonitrile (15 to 90%) in 0.1% TFA, and then either analyzed by SDS-PAGE under denaturing and reducing conditions (Laemmli, 1970) or digested with sequencing grade trypsin or endoproteinase Asp-N according to the manufacturer's instructions (Boehringer Mannheim). Peptide fragments of the digested protein were separated on a C18 reverse phase HPLC column (2.1×150 mm, Vydac) in a linear gradient (0 to 90%) of acetonitrile in 0.1% TFA, and sequenced in a pulse liquid sequencer (Applied Biosystems 477A).

In order to generate a probe with which to screen cDNA libraries, degenerate coding [5',-GGCGAATTCGA(TC)GC-(GATC)AT-(ATC) TT(TC)AA(GA)GA-3'] (SEQ ID NO:05) and noncoding [5'-GGCAAGCTT(GA)TC-(GATC) A(GA)(TC)TT(TC)TC(GATC)GC(TC)TG-3'] (SEQ ID NO:06) primers containing all possible codons of the 6 amino acids at the amino- and carboxyl-termini of a 30 amino acid sequence deduced from peptide fragments of the purified protein were synthesized. These primers were used in a polymerase chain reaction (PCR) containing first strand cDNA, synthesized from poly(A)$^+$-selected rat liver RNA using the degenerate noncoding primer, as template. The expected 108-bp PCR product was gel isolated, subcloned into Bluescript KS+ (Stratagene) at the Eco RI and Hind III sites, and sequenced to confirm that it correctly predicted the internal 18 amino acids of the original peptide sequence.

A small amount of the gel-purified 108-bp PCR product was used as template in a subsequent PCR reaction containing 20 μM dNTPs, including 100 μCi of [α-$^{32}$P]dCTP to label the PCR product internally. The $^{32}$P-labeled 108-bp PCR product was used to screen a random- and oligo dT-primed rat liver cDNA library (Stratagene) under stringent conditions (65° C. wash in 0.1× SSC). Twenty individual clones were isolated from an initial screen of 600,000 plaques. Partial sequences of the 20 clones revealed that they encoded the same protein. The largest insert, designated M1, was sequenced completely.

The 949-bp M1 insert, labeled with $^{32}$P by random priming, was used to screen an oligo dT-primed mouse liver cDNA library (Stratagene) and an oligo dT-primed HepG2 human hepatoma cDNA library (Stratgene) under lower-stringency conditions (45° C. wash in 1× SSC). Positive clones, isolated from these two libraries also at a frequency of about 1 in 30,000, were treated as described for the clones isolated from the rat liver library. The two largest inserts (10E3B from the mouse library and 4.1 from the human library) were sequenced completely.

RNA analysis

Total RNA was prepared from adult rat and mouse tissues and from cell lines lysed in guanidinium isothiocyanate as previously described (Chirgwin et al.1979). Northern blot analysis of rat liver RNA was performed according to standard conditions (Alwine et al.1977; Thomas, 1980). Briefly, 10 μg of total rat liver RNA was electrophoresed in a 1.5% agarose gel containing formaldehyde, and the RNA transferred to nitrocellulose. The RNA was covalently crosslinked to the nitrocellulose in a Stratalinker (Stratagene). The filter was then incubated overnight at 42° C. in prehybridization solution containing 50% formamide, 5×SSC, and 50 μg/ml sonicated salmon sperm DNA, and then hybridized overnight under the same conditions in prehydridization solution containing 5×10$^5$ cpm/ml of the 949-bp M1 insert labeled with $^{32}$P by random priming. The blot was washed twice in 2×SSPE at 55° C. for 15 min each time, and twice in 0.2×SSPE at 55° C. for 15 min each time. The nitrocellulose filter was then dried and exposed to film at −70° C. in the presence of an intensifying screen.

Ribonuclease protection assays were performed as previously described (Baumhueter et al.1988; Mendel et al.1991). The constructs used to generate antisense riboprobes with which to detect mouse or rat DCoHmRNA were prepared as follows. The M1 and 10E3B HNF inserts in Bluscript SK- (Stratagene) were cut with Sty I and Hinc II, the Sty I overhang filled in with Klenow enzyme, and the blunt ends of the plasmids religated. The reclosed plasmids were linearized with Pst I, and antisense riboprobes transcribed in the presence of [α$^{32}$P]UTP using T7 RNA polymerase. Full length riboprobes were gel-purified and used in RNase protection assays using 10 μg of total RNA, or tRNA as negative control, and 2–5×10$^5$ cpm of riboprobe. The protected region of the rat DCoH message is 227 nt, corresponding to nucleotides 398–624 of the M1 sequence. The protected region of the murine DCoH message is 208 nt, corresponding to a region of the 10E3B sequence similar to the region of M1 sequence protected by the rat riboprobe.

In Vitro Transcription and Translation

The EcoRI/EcoRV fragment (nt 1–2174, (Kuo et al.1990)) encoding the entire open reading frame of murine HNF-1α was subcloned into pBluscript KS+ (Stratagene) cut with EcoRI and EcoRV (pHNF-1α RI/RV). Full length HNF-1α message was transcribed from pHNF-1α RI/RV linearized with HindIII. Message for the carboxyl terminal deletions was transcribed from pHNF-1α RI/RV linearized with AhaII (Δ429–628), BalI (Δ282–628), or AlwNI (Δ214–628). The construct encoding HNF-1α without the 30-amino acid dimerization domain (Δ2–30) was constructed as described for HNF-1β (Mendel et al.1991) by PCR using pHNF-1α RI/RV insert as template and a coding primer, 5'-GCCGAATTCGGAGCCATGGGGGAGC-CAGG-3' (SEQ ID NO:07), which encodes a start methionine followed by amino acids 31–34 of HNF-1α in the context of the natural HNF-1α Kozak sequence (Kozak, 1986), and a noncoding primer corresponding to a sequence near the homeodomain of HNF-1α. The PCR product was cut with EcoRI and MluI, and the 127-bp EcoRI/MluI fragment inserted into pHNF-1α RI/RV that had been cut with EcoRI and MluI. The first 200 bp of the final construct were sequenced to insure that there were no amino acid substitutions during the PCR amplification step, and to insure that the open reading frame remained intact at the MluI site. The first seven amino acids encoded by this construct are (SEQ ID NO:08) M/GEPGPY. A plasmid encoding HNF-1α with an internal deletion of amino acids 29–67 was constructed using restriction sites in the HNF-1α sequence. pHNF-1α RI/RV was cut with MluI, the overhang filled in, and a 1781-bp fragment cut out with HindIII. This fragment was subcloned into pHNF-1α RI/RV cut with StuI and HindIII. The resulting construct encoded an HNF-1α molecule lacking amino acids 29–67, but with no amino acids added. The amino acid sequence at the junction is (SEQ ID NO:09) SKEALIQA/RGSEDD. Message encoding full length HNF-1β was transcribed from a template containing the full open reading frame of HNF-1β but none of the 5' untranslated region (Mendel et al.1991). This template was linearized with EcoRI. Message for the carboxyl-terminal truncations of HNF-1β was transcribed from this template linearized with BstEII (Δ346–532) or HincII (Δ185–532). The template encoding HNF-1β without the 30 amino acid dimerization domain (Δ2–30) has been previously described (Mendel et al.1991), and was linearized with EcoRI. The template encoding DCoH was constructed by subcloning a 777-bp SacII/EcoRI fragment of the M1 insert, corresponding to nucleotides 172–948, into pBluescriptKS+. This construct was linearized with BstEII.

Capped transcripts were generated from all constructs in 30-µl reactions containing 1–2 µg of linearized plasmid and 20–40 units of T7RNA polymerase (Boehringer Mannheim) according to the manufacturer's instructions. After transcription, RNA was extracted once with phenol/chloroform and once with chloroform, precipitated twice with ethanol in the presence of 2M ammonium acetate using 20 µg glycogen as carrier, and dissolved in 20 µl water. Approximately one-tenth of the capped RNA from each reaction was then translated for 90 min at 30° C. in a rabbit reticulocyte translation reaction (25 µl) or, in the case of HBF alone, for 90 min at room temperature in a wheat germ lysate translation reaction (25 µl). Translation reactions were performed according to the manufacturer's instructions (Promega) in the presence of [$^{35}$S]methionine.

Assay of the stability of the HNF-1α dimer to exchange

Gel retardation assays were performed as previously described (Fried and Crothers, 1981; Strauss and Varshavsky, 1984) using the β28 probe, a 28-bp double-stranded, blunt-ended oligonucleotide based on the sequence of the HNF-1 site in the promoter for β-fibrinogen (Fowlkes et al., 1984; Courtois et al., 1987). A typical reaction contained approximately 20,000 cpm (~0.2 ng) of the kinased β28 probe in a 20-µl volume containing 10 mM Tris (pH 7.8), 50 mM KCl, 1 mM DTT, 0.1 mM EDTA, 5% glycerol, 100 ng of poly [d(IC)], and 5 µl of translated protein. Samples containing rat liver nuclear extract, prepared as previously described (Courtois et al., 1987), contained 3.5 µg of nuclear protein and 1 µg of poly [d(IC)]. DNA-protein complexes were allowed to form for 30–60 min at room temperature before being resolved on 4% nondenaturing acrylamide gels in 1×TBE buffer at 10 V/cm. After electrophoresis, gels were fixed in 20% methanol, 10% acetic acid, dried, and exposed to film at −70° C. in the presence of an intensifying screen. The dried gels were separated from film by an intensifying screen to shield the film from exposure by $^{35}$S.

Challenge experiments, designed to test whether the subunits of the HNF-1 dimer could exchange, were performed as follows. 2.5 µl of an in vitro translation reaction primed with message for full length HNF-1α or β, either by itself or in addition to message for DCoH, was mixed with an equal volume of a separate in vitro translation reaction primed with RNA encoding truncated HNF-1α or β, or without RNA. The mixed reactions were left at room temperature for 60 min to allow the subunits of the HNF-1 dimers to dissociate and reassociate prior to the addition of the β28 probe.

Measurements of the rate of dissociation of HNF-1α from the β28 probe were performed as follows. Rat liver nuclear extracts or HNF-1α translated in the absence of presence of DCoH was incubated for 30–60 min at room temperature with ~0.2 ng of $^{32}$P-labeled β28 probe in a typical gel retardation assay reaction. 20 ng of nonradioactive β28 oligonucleotide was then added to the reaction and 20-µl samples of the reaction loaded onto a running nondenaturing acrylamide gel at various time points after the addition of the nonradioactive oligonucleotide.

Immunoprecipitation

Rabbit antisera directed against HNF-1α or HNF-1β have been described previously (Mendel et al.1991). Two additional antisera directed against HNF-1α, generated by injecting mice with synthetic peptides coupled to Keyhole Limpet hemocyanin, were also used in this study. One antisera was generated against synthetic peptides corresponding to amino acids 96–121 and 225–249 of HNF-1α; the other was directed against these two peptides plus a third peptide corresponding to amino acids 1–30 of HNF-1α.

Antibody (1 µl of antisera), pre-absorbed to Pansorbin (1.5 µl of slurry) (Calbiochem) in the presence of PBS containing BSA (1 mg/ml) and washed twice with PBS, was added to in vitro translation reactions (25 µl) and left at 4° C. for 2 hr with occasional mixing. The Pansorbin containing the antibody-protein complexes was then centrifuged at 11,000×g, the supernatant removed, and the Pansorbin washed 2 times in 200 µl cold PBS. Antibody-protein complexes were eluted from the Pansorbin by resuspending the washed pellet in 25 µl SDS-PAGE sample buffer (Laemmli, 1970) and heating the suspension for 3 min in a boiling water bath. Following centrifugation to pellet the Pansorbin, the soluble sample was electrophoresed on an SDS-PAGE mini gel (14% acrylamide) run under denaturing and reducing conditions. Gels were fixed in 20% methanol, 10% acetic acid and stained with Coomassie Blue using standard conditions. Radioactivity in the gels was visualized by fluorography using 0.5M sodium salycilate as scintillant (Northrop et al., 1985).

To accurately determine the relative amounts of HNF-1α and DCoH precipitated, the radioactivity in the dried gel was directly quantitated using an AMBIS radioactivity scanner. Equal areas of the gel, corresponding to the migration position of the HNF-1α and DCoH in a given sample, were quantitated. Measurements of background radioactivity were determined for an equal area in a sample containing DCoH translated and precipitated with the rabbit antiserum against HNF-1α. The background value taken for HNF-1α was determined at the position at which full length HNF-1α would have migrated; the background value for DCoH was determined at the migration position of the DCoH that non-specifically adsorbed to the Pansorbin.

Generation of GAL4 fusion proteins

A construct encoding the DCoH-GAL4-VP16 fusion protein was generated by overlap extension PCR (Horton et al., 1989; Ho et al., 1989). Briefly, overlapping coding (5'-GTCTATGAC-AATGAAGCTACTGTC-3') (SEQ ID NO:10) and noncoding (5'GTAGCTTCATTGTCA-CGG-3') (SEQ ID NO:10) primers were synthesized to encode the last few amino acids of DCoH and the first few amino acids of GAL4. These primers were used in PCR reactions containing a coding primer (5'-GGCCGAATTCGCACTGGA-CATGGCTCCAAG-3') (SEQ ID NO:12) or a noncoding primer (5'-GGCCGAATTCTACGATACAGTCAACTG-3') (SEQ ID NO:13) encoding the first 4 amino acids of DCoH and amino acids 143–147 of GAL4, respectively, and the M1 insert or the pJL2 plasmid (Chasman et al., 1989), encoding GAL4(1–147)-VP16 (Sadowski et al., 1988), as template. This procedure produced an open reading frame encoding the full 104 amino acids of DCoH fused to the amino terminus of amino acids 1–147 of GAL4. The Eco RI-XhoI fragment containing most of the PCR product was subcloned into pBluescript KS+ (interim plasmid I). The insert of interim plasmid I was sequenced to insure that no mutations were introduced during the amplification steps. The predicted sequence at the DCoH-GAL4 Junction is VAVSMT/MKLLSS (SEQ ID NO:14). The XhoI-HindIII fragment of pJL2, encoding the carboxyl end of GAL4-VP16, was also subcloned into pBluescript (interim plasmid II). A plasmid, pDCoH-GAL4-VP16, containing an open reading frame encoding the full DCoH-GAL4-VP16 fusion protein was constructed in pBluescript by subcloning an XhoI-PvuII fragment of interim plasmid II into interim plasmid I cut with Asp718, the site blunted, and then cut with XhoI.

The GAL4(1–147) expression vector was constructed by inserting the 450-bp MscI-Eco RI fragment of pDCoH-GAL4-VP16 into pBJ5 (see below) cut with XhoI, the site blunted, and then cut with Eco RI. The DCoH-GAL4 expression vector was constructed by inserting the 800-bp Eco RI fragment of pDCoH-GAL4-VP16 into pBJ5 cut with Eco RI. The GAL4-VP16 expression vector was constructed by inserting the 1 kb MscI-NotI fragment of pDCoH-GAL4-VP16 into pBJ5 cut with XhoI, the site blunted, and then cut with NotI. The DCoH-GAL4-VP16 expression vector was constructed by inserting the 1.3 kb NotI-Eco RV fragment of pDCoH-GAL4-VP16 into pBJ5 cut with Eco RI, the site blunted, and then cut with NotI. All constructs contained start methionines preceded by appropriate Kozak sequences (Kozak, 1986).

Transient transfection studies

The murine HNF-1α and HNF-1β expression vectors constructed in the Srα-based pBJ5 expression vector have been described previously (Kuo et al., 1990; Mendel et al., 1991). The DCoH expression vector was constructed by inserting the 949-bp M1 cDNA into the pBJ5 expression vector at a unique Eco RI site. The RSV-luciferase plasmid (Courtois et al., 1987), the pRSVrGHF1 expression vector (Theill et al., 1989), the pRSVmRec mouse glucocorticoid receptor expression vector (Danielsen et al., 1986), and the (β28)$_3$-CAT (Kuo et al., 1990), –289hGHCAT (Lefevre et al., 1987), MMTVCAT (Danielsen, et al., 1986), and GAL4$_5$ElbCAT (Lillie and Green, 1989) reporter constructs have been described previously. The αFg-CAT reporter construct consists of a ~500-bp fragment of the α-fibrinogen promoter driving the CAT gene.

For each data point, 0.5–1×10$^7$ CHO or COS cells were transfected with the indicated amounts of the expression and reporter constructs by electroporation using a Bio-Rad Gene Pulser set at 960 µF and 230 V. Transfections were performed in duplicate or triplicate, and 2 µg of the RSV-luciferase plasmid was included in each sample as an internal control for transfection efficiency. The total amount of DNA transfected into each sample of a given experiment was held constant by including an appropriate amount of pBJ5 expression vector lacking an insert. CAT (Gorman et al., 1982) and luciferase (de Wet et al., 1987) activity were measured 36–48 hours after transfection. CAT assays were quantitated on an AMBIS radioactivity scanner, and the amount of CAT activity in each sample was corrected for transfection efficiency based on the results of the luciferase assay.

Figure Legends

Figure 1A:
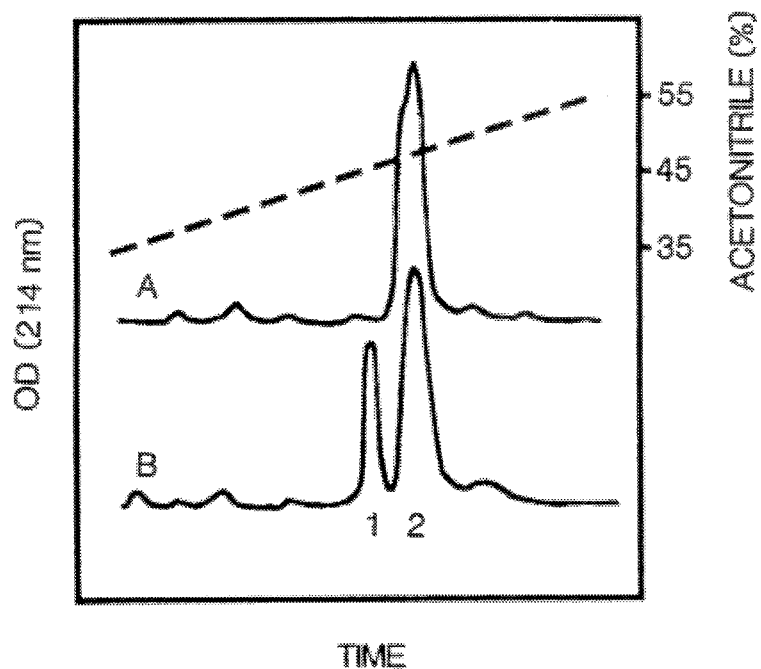
FIG. 1a is the elution profile of HNF-1α from a DNA affinity column.

FIG. 1. DCoH is an ~11-kDa protein that co-purifies with HNF-1α. (A) HNF-1α, as it eluted from the DNA affinity column (trace A) or after being denatured and alkylated (trace B), was eluted from a C8 reverse phase HPLC column in a linear acetonitrile gradient (dashed line). Protein was monitored at 214 nm. (B) Protein eluted from the C8 column was visualized on silver-stained SDS-PAGE gels (10–20% linear gradient). Samples contain: (lane A), the protein from the single major peak in trace A; (lane B1), the protein in peak 1 of trace B; (lane B2), the protein in peak 2 of trace B. The migration position of molecular weight markers are shown to the right. (C) Nucleotide sequences of the M1 (rat) (SEQ ID NO:01) 10E3B (mouse) 3, and part of the 4 (human) 2 inserts are shown along with the predicted amino acid sequence of the rat DCoH (DCoH) protein (SEQ ID NO:04) Nucleotides in the open reading frame of the human and mouse clones which correspond to the nucleotides of the rat sequence are indicated with dashes. Amino acids not determined from the purified protein are single underlined. The 30-amino acid peptide sequence used to generate the 108-bp PCR product is double underlined. The conservative substitution of a valine in the mouse protein for a leucine at residue 28 of the rat protein is indicated.

FIG. 2. DCoH directly interacts with HNF-1α and HNF-1β. DCoH was co-translated with various HNF-1α or HNF-1β mutants in the presence of [$^{35}$S]methionine. Following translation, HNF-1 molecules and associated proteins were immunoprecipitated with antibodies directed against HNF-1α or HNF-1β, separated on SDS-PAGE gels, and visualized by fluorography (right). The ability of DCoH to bind to a given HNF-1 mutant was evaluated based on whether DCoH, which could be detected when translated by itself in a wheat germ lysate (lane 13), was present in the immunoprecipitated complex. Lanes 1–6 and 9–12 contain immunoprecipitated samples from co-translations containing different HNF-1α and β constructs, respectively. The HNF-1α and HNF-1β mutants, generated by carboxyl-terminal truncations or internal deletions of the full length clones, are depicted schematically (left), with the previously identified functional regions of the HNF-1 molecules indicated by shading; dimerization domain (medium shading), POU motif (light shading), extended homeodomain (dark shading). Full length HNF-1α and β are depicted in constructs 1 and 9, respectively. To evaluate whether DCoH is precipitated non-specifically, antibody directed against HNF-1α or HNF-1β was used to precipitate DCoH translated in the absence of HNF-1 (lanes 7 and 8, respectively). The migration position of in vitro translated DCoH and the molecular weight standards are indicated.

Figure 3A:
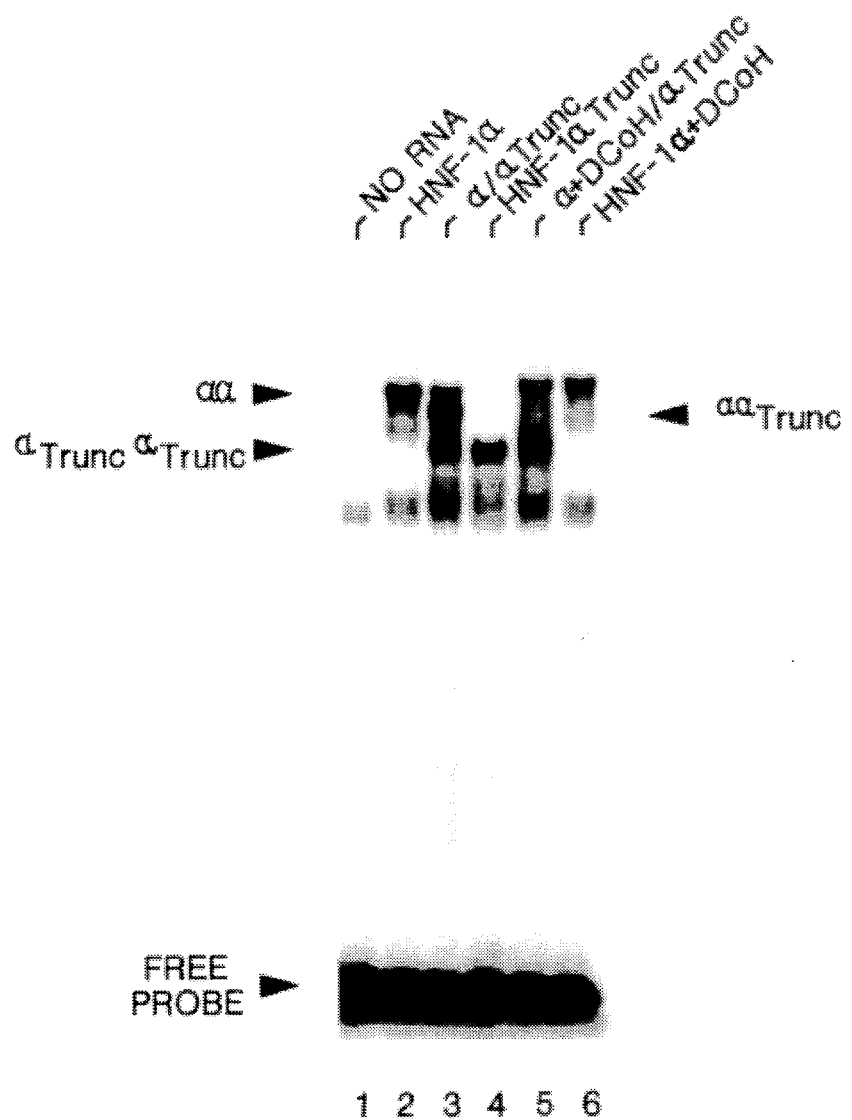
FIGS. 3a, b and c are visualized non-denaturing PAGE gels evaluating binding of DCoH to HNF-1α or truncated forms of HNF-1α in the presence of RNA.
Figure 3B:
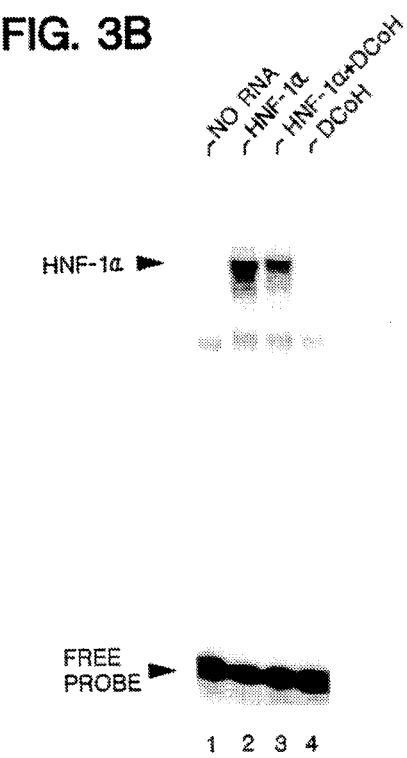
Figure 3C:
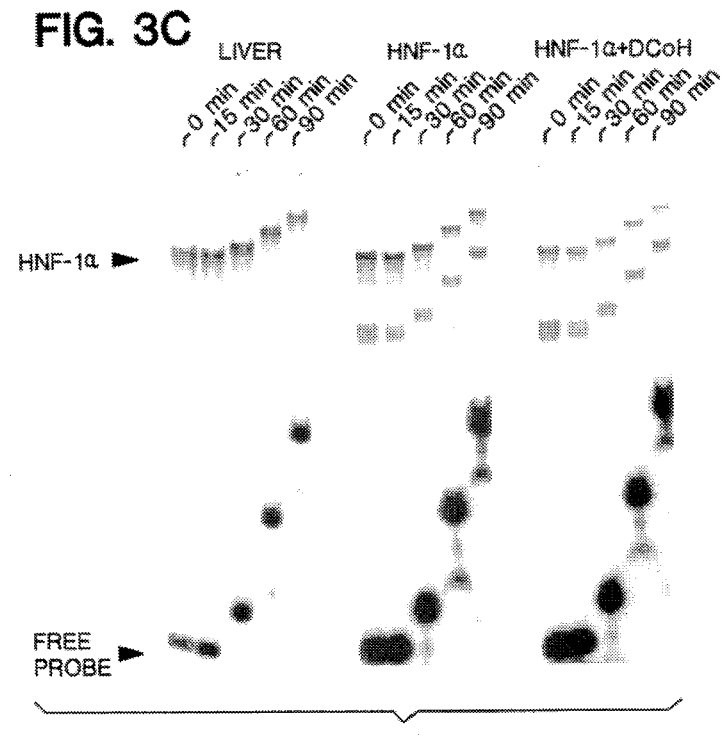

FIG. 3. DCoH stabilizes the HNF-1a dimer. (A) Messeger RNA encoding full length HNF-1α was translated in vitro by itself (HNF-1α) or cotranslated with mRNA encoding DCoH (HNF-1α+DCoH). The translated protein was mixed with an equal volume of a translation reaction primed with RNA encoding a truncated form of HNF-1α lacking the last 200 amino acids (HNF-1$α_{Trunc}$). The mixture containing full length HNF-1α is indicated as α/$α_{trunc}$; the mixture containing full length HNF-1α translated in the presence of DCoH is indicated as α+DCoH/$α_{Trunc}$. After 60 min, $^{32}$P-labeled β28 probe was added to the reaction, and the DNA-protein complexes resolved by nondenaturing polyacrylamide gel electrophoresis. The migration position of homodimers of full length HNF-1α (αα), truncated HNF-1α ($α_{Trunc}α_{Trunc}$), and heterodimers of full length and truncated HNF-1α (α$α_{Trunc}$), as well as the migration position of the free probe are indicated. The protein-DNA complex visible in the translation reaction that was not primed with RNA (No RNA) indicates the presence of a non-specific complex which is present in variable amounts in all the samples. (B) DCoH does not bind to the HNF-1 site and does not enhance the binding of HNF-1α to the HNF-1 site. Message RNA for HNF-1α, for DCoH, or for a mixture of the two (HNF-1α+DCoH) was translated in vitro and assayed for binding to the β28 probe. The migration position of the HNF-1α complex and of the free probe are indicated. Slightly less HNF-1α protein was produced in the translation reaction containing a combination of the messages for HNF-1α and DCoH (data not shown). (C) DCoH does not stabilize the HNF-1α-DNA complex. $^{32}$P-labeled β28 probe was added to rat liver nuclear extract (LIVER), or to translation reactions primed with message for HNF-1α alone (HNF-1α) or in addition to message for DCoH (HNF-1α+DCoH). After 30 min, excess unlabeled β28 oligo was added, and aliquots of the reaction loaded onto a running non-denaturing polyacrylamide gel after the indicated time of incubation with the unlabeled β28 oligonucleotide. The migration positions of the HNF-1α-DNA complex and the free probe, for a sample loaded onto the gel immediately after adding the unlabeled oligo, are indicated. As in (B), slightly less HNF-1α protein was produced in the translation reaction containing both messages than in the reaction containing only the message for HNF-1α.

Figure 4A:
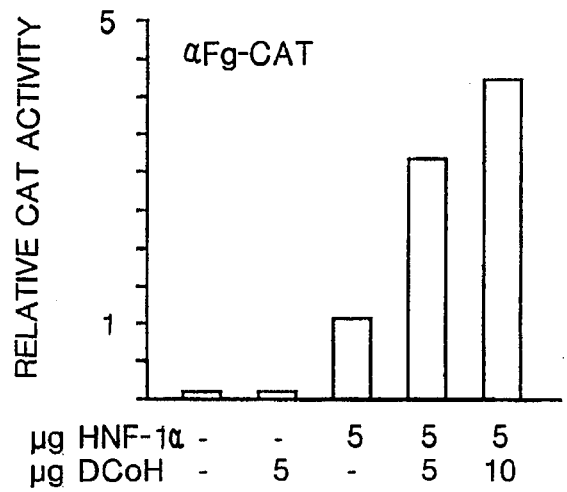
FIGS. 4a, b and c are bar graphs evaluating the binding of HNF-1α and DCoH as evidenced by CAT expression.
Figure 4B:
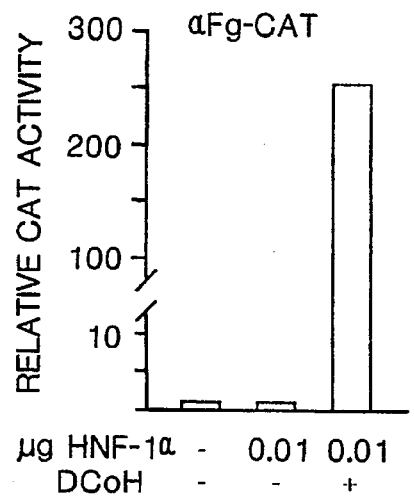
Figure 4C:
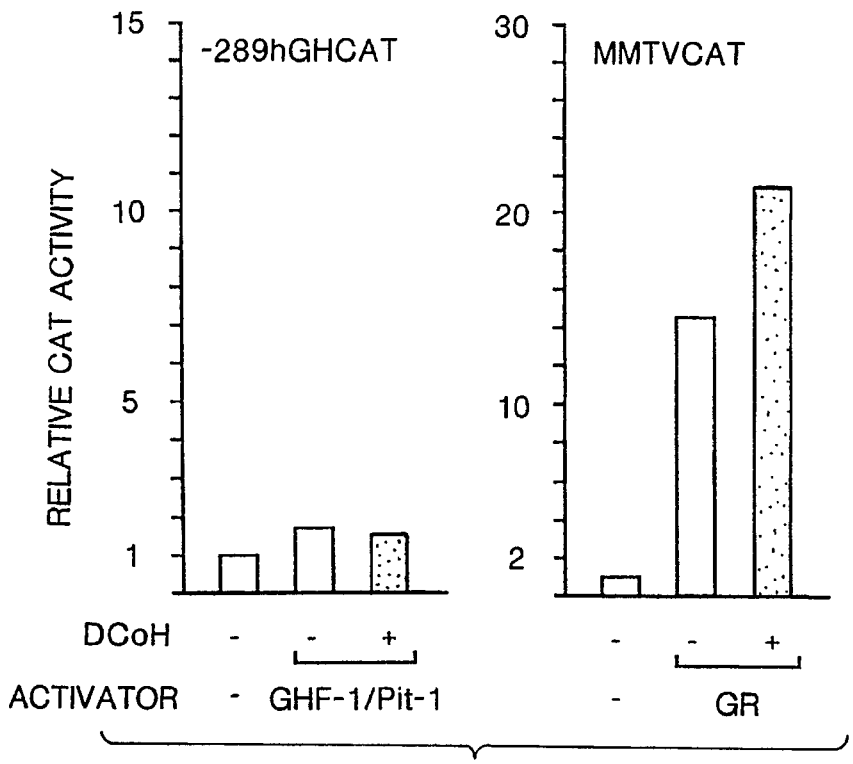

FIG. 4. Selective enhancement of the transcriptional activity of HNF-1α by DCoH. The CHO cells were transfected (see above) with (A) the αFg-CAT reporter construct (5 μg) and the indicated amounts of the expression vectors encoding HNF-1α and DCoH; (B) the αFg-CAT reporter construct and 10 ng of the HNF-1α expression vector in the presence or absence of the DCoH expression vector (1 μg); or (C) the expression vector for the indicated activator protein and reporter construct either in the absence (open bars) or presence (shaded bars) of DCoH expression vector. Cells were assayed for CAT activity 36 to 48 hours after transfection. Results are presented as the averages of duplicate measurements in a representative experiment and are corrected for transfection efficiency (Horton etal., 1989; Ho et al., 1989).

Figure 5:
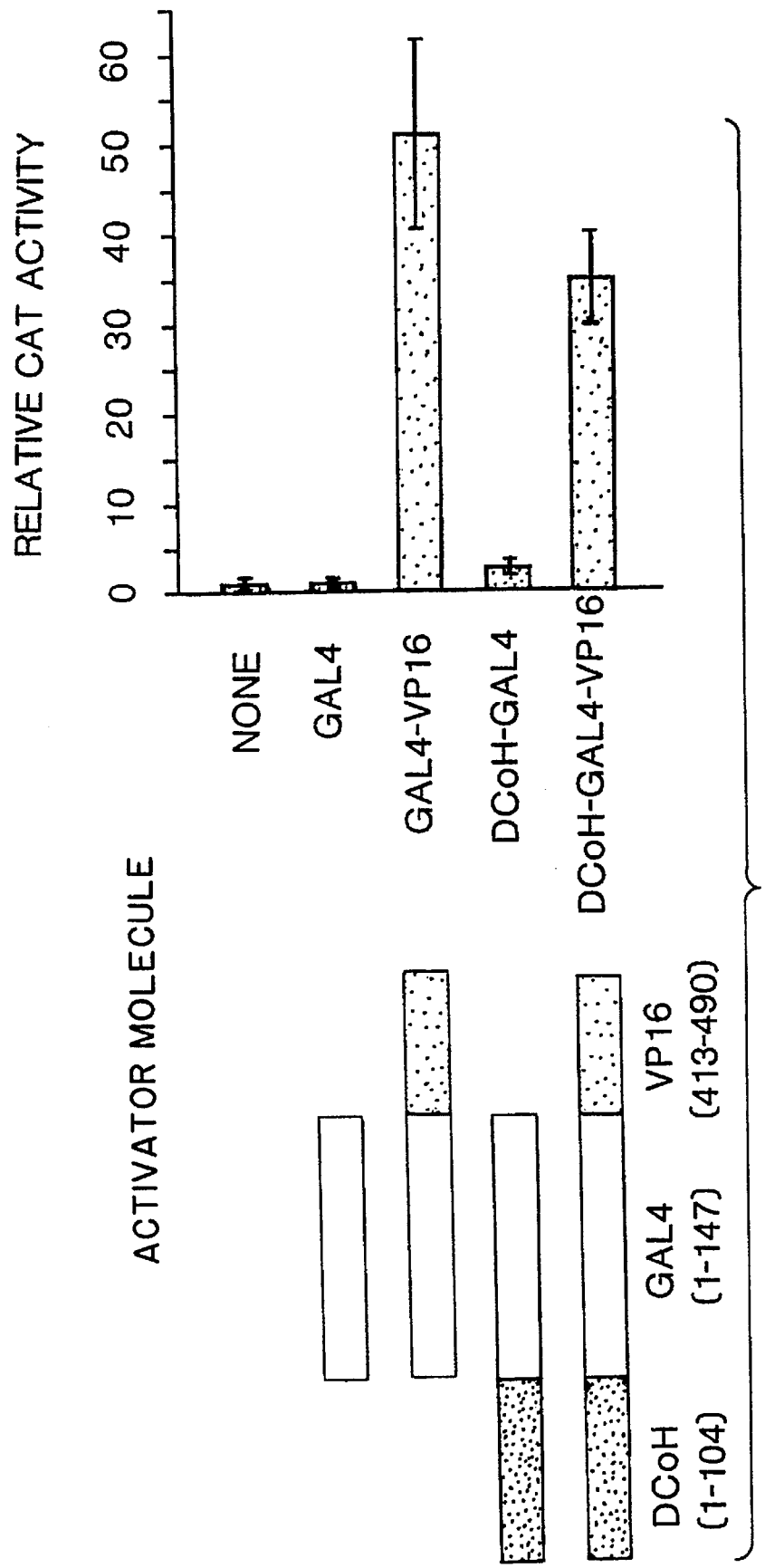
FIG. 5 diagrams fusion protein constructs and their activity as determined by CAT expression.

FIG. 5. DCoH does not confer transcriptional activity to a DNA binding domain. CHO cells were co-transfected with 15 μg of the $GAL_5$ E1B-CAT reporter construct containing five tandemly linked GAL4 binding dites directing transcription of the CAT gene and 15 μg of an expression vector encoding the indicated fusion protein containing the GAL4 dimerization and DNA binding domain. The protein encoded by each of the expression vectors is shown schematically to the left, where the open box represents the dimerization and DNA binding domain of GAL4 (amino acids 1–147 of GAL4), the lightly shaded box represents the 78-amino acid acidic activation domain of VP16 (amino acids 413–490 of VP16), and the darkly shaded box represents the entire 104 amino acid sequence of DCoH. Results are calculated and presented as indicated in the legend to FIG. 4.

Figure 6A:
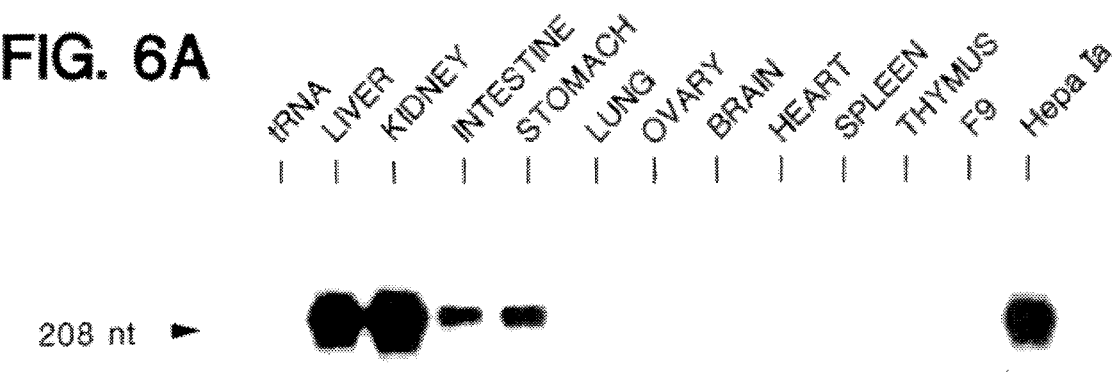
FIGS. 6a and b are visualized gels of RNA from various organs or cell lines probed for the presence of DCoH message.
Figure 6B:
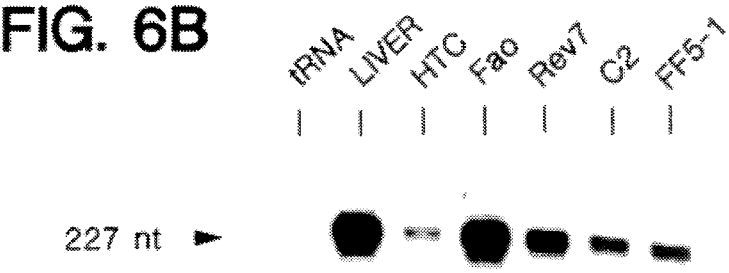

FIG. 6. DCoH message is expressed in tissues and cells which express the message for HNF-1α or HNF-1β. 10 μg of total RNA from the indicated tissues and cell lines was examined for the presence of DCoH message in a ribonuclease protection assay. DCoH message was indicated by the presence of a 208-nt, or 227-nt, radioactive fragment in mouse, (A) and (C), or rat, (B), samples, respectively. 10 μg of tRNA was used as a negative control in each experiment.

TABLE 1

IMMUNOPRECIPITATED COMPLEXES CONTAIN TWO DCoH MOLECULES AND TWO HNF-1$_α$ MOLECULES.[1]

| HNF-1$_α$ CONSTRUCT[2] | HNF-1$_α$ | | | DCoH | | DCoH:HNF-1[5] |
| --- | --- | --- | --- | --- | --- | --- |
| | NUMBER OF METHIONINES[3] | RAW COUNTS | CORRECTED COUNTS[4] | RAW COUNTS | CORRECTED COUNTS[5] | |
| 1 | 13 | 18,458 | 16,421 | 9,998 | 2,610 | 0.69 |
| 1 | 13 | 52,891 | 50,854 | 25,077 | 17,689 | 0.66 |
| 1 | 13 | 25,844 | 23,807 | 11,321 | 3,933 | 1.40 |
| 2 | 12 | 20,489 | 18,452 | 7,060 | −280 | 0 |
| 4 | 7 | 88,100 | 86,063 | 49,012 | 41,624 | 1.12 |
| 5 | 4 | 34,323 | 32,286 | 40,146 | 32,758 | 1.35 |
| 6 | 4 | 59,693 | 57,656 | 70,654 | 63,266 | 1.47 |

1. Numerical data presented in this table was obtained by direct quantitation of the radioactivity in the gel shown in FIG. 2 using an AMBIS radioactivity scanner.

2. HNF-1α construct numbers are the same as those associated with the schematic representations shown in FIG. 2. There are three separate constructs with the number 1 to indicate separate results obtained using different antibodies to precipitate the full length HNF-1α:DCoH complex. The first values were obtained from the sample shown in lane 1 of FIG. 3. The second values are from a duplicate sample precipitated with a second antiserum to HNF-1a, generated against synthetic peptides corresponding to amino acids 96–121 and 225–249 of HNF-1α. This antiserum was used to precipitate samples 4 through 6. The third values are from a duplicate sample precipitated with a third antisera to HNF-1α, generated against synthetic peptides corresponding to amino acid sequences 1–30, 96–121, and 225–249 of HNF-1α.

3. The number of methionines in each HNF-1α construct was determined from the predicted amino acid sequence of the mouse HNF-1α cDNA (Kuo et al., 1990). The DCoH construct contains 3 methionines (see FIG. 1C).

4. Raw counts were corrected by subtracting out a background value as described in the Experimental Procedures. Background values were 2037 counts for HNF-1α, and 7388 counts for DCoH.

5. The stoichiometric ratio of DCoH molecules to HNF-1α molecules in the precipitated complexes was determined from the corrected counts and the number of methionines in each construct using the formula:

molecules DCoH (Corrected counts$_{DCoH}$)/3 molecules HNF-1α(Corrected counts$_{HNF-1\alpha}$) / (number of methionines)

Results

The purified HNF-1α migrated as a single broad band on 8% or 10% SDS-PAGE gels, but consistently eluted from a C8 reverse phase HPLC column as a single major peak, but with a shoulder on the leading edge of the eluted peak. By denaturing and pyridinylating the purified HNF-1α prior to loading it on the C8 column, the shoulder was clearly resolved from the major peak. Microsequencing and SDS-PAGE analysis of the protein contents of the resolved peaks indicated that the major peak contained exclusively HNF-1α, and that the shoulder contained a single approximately 11-kDa protein, which was not a proteolytic fragment of HNF-1α.

Sequence data obtained from the purified approximately 11-kDa protein called Dimerization Cofactor for HNF-1 ("DCoH") provided five peptide sequences ranging in size from 11–30 amino acids, which contained a total of 95 amino acids. Twenty individual cDNA clones were isolated encoding DCoH in an initial screen of 600,000 plaques from a rat liver cDNA library. The open reading frame of the longest insert, designated M1, encoded all five peptide sequences deduced from the purified DCoH protein, confirming 95 of the 104 predicted amino acids (see complete sequence in FIG. 1). The M1 insert is comparable in size to the single mRNA identified by Northern blot analysis of rat liver RNA using the M1 insert as probe under high astringency conditions, supporting the observation that the M1 insert contains most of the message for DCoH. The M1 insert was used to screen mouse liver and human hepatoma cDNA libraries to obtain clones encoding murine and human DCoH. Although none of the cDNA clones isolated from these libraries encoded the entire open reading frame of DCoH, the deduced amino acid sequences of murine and human DCoH were remarkably similar to that of rat DCoH, with only a single conservative substitution (a valine in the murine, protein replaces the leucine at residue 28 of the rat protein) among the three predicted amino acid sequences. The higher degree of conservation of the DCoH amino acid sequence among the three species supports the conclusion that the entire DCoH protein is required for the function(s) of DCoH.

The predicted amino acid sequence of DCoH does not contain any previously identified DNA-binding motif, nor does it contain a clustering of basic residues which might mediate direct binding to DNA. Antibodies directed against HNF-1α were employed to see whether DCoH would be coprecipitated as part of a complex following translation of the two proteins in vitro. The results demonstrated that the antibodies to HNF-1α precipitated DCoH only when HNF-1α was present in the reticulocyte lysate. Since these experiments were performed in the absence of HNF-1 DNA-binding site, the interaction between these two proteins does not depend on HNF-1α binding to its recognition sequence.

To investigate the specificity of this interaction, a series of truncations and internal deletions of HNF-1α were examined. Carboxyl terminal deletions of HNF-1α, including one that removes the homeodomain, do not reduce the binding of DCoH. However, removal of the amino terminal 30 residues which constitute a dimerization domain in HNF-1α (Nicosia et al., 1990, Chouard et al., 1990) eliminates the DCoH-HNF-1α interaction. And internal deletion of the 35 amino acids immediately following the dimerization domain has little effect on DCoH binding to HNF-1α, indicating that the protein-protein interaction is not unduly sensitive to conformational changes which might be caused by deletions near the amino terminus of the protein. Using [$^{35}$S] methionine to obtain radiolabeled DCoH and HNF-1α, the relative stoichiometry of DCoH and HNF-1α in the precipitated complexes based on direct quantitation of their radioactivity in the bands associated with HNF-1α and DCoH following SDS-PAGE were determined (Table 1). Although the amount of precipitated HNF-1α varied, a relatively constant ratio of 1.1 (±0.36) DCoH molecules per molecule of HNF-1α was observed. In combination with the previous determinations that HNF-1α s a dimer, it may be concluded that the precipitated complexes are hetero-tetramers containing two molecules of HNF-1α and two molecules of DCoH. Results indicate that in the absence of HNF-1α, DCoH is a dimer, supporting the conclusion that the tetrameric complex is composed of a DCoH dimer bound to an HNF-1α dimer.

To test whether HNF-1β, a homologue of HNF-1α which is closely related to HNF-1α between its amino-terminal dimerization domain and homeodomain, would also bind to DCoH, the following investigation was carried out as previously described. Mutants that lacked the dimerization domain of HNF-1β were unable to interact with DCoH. Carboxyl-terminal truncations of HNF-1β bound DCoH as well as the full length protein, including one truncation that removes a charged region of HNF-1β similar in sequence to the POU-specific region of the POU homeodomain (Herr, et al., 1988). This region of the POU homeodomain has been implicated in protein-protein interactions between members of the POU subfamily of homeodomain-containing proteins (Ingraham et al., 1990; Voss et al., 1991; Treacy et al., 1991).

To test whether DCoH can stabilize the HNF-1α dimer, a truncated form of HNF-1α was used, the truncated form contained the first 428 amino acids of HNF-1α . The truncated form was used to challenge the full length of HNF-1α dimer translated in vitro in the presence or absence of DCoH. It was previously reported, that the HNF-1α dimer translated in Vitro is unstable and, upon challenge with the truncated HNF-1α, the subunits of the dimer reassociate as homodimers of full length HNF-1α (αα), homodimers of truncated HNF-1α ($\alpha_{Trunc}\alpha_{Trunc}$), and heterodimers of full length and truncated HNF-1α ($\alpha\alpha_{Trunc}$). The full length homodimers, the heterodimers and the truncated homodimers are present with an apparent abundance of 1:2:1 respectively, indicating that these complexes are unrestricted in terms of their ability to associate with each other (Hope et al., 1987). In marked contrast, the HNF-1α dimer translated in the presence of DCoH is stable, as indicated by the observation that there is a substantial reduction in the amount of heterodimers formed when the cotranslated agent HNF-1α:DCoH complex is mixed with truncated HNF-1α. The slightly slower migration of the full length HNF-1α homodimer translated in the presence of DCoH relative to that of HNF-1α translated alone is reproducible and is consistent with the presence of the two molecules of DCoH bound to the HNF-1α dimer.

Cotranslation of HNF-1α and DCoH does not result in more binding activity than when HNF-1α is translated alone as evidenced by binding to the β28 probe. Similarly, DCoH does not stabilize the interaction between HNF-1α and its recognition sequence as indicated by the observation that a dissociation rate of HNF-1α, measured at room temperature, does not differ between native HNF-1α from liver nuclear extract and HNF-1α translated in vitro in the presence or absence of DCoH.

The effect which DCoH has on the transcriptional activity of HNF-1α in vivo was determined by testing the activity of HNF-1 dependent promoters cotransfected into recipient cells along with expression vectors for HNF-1α or HNF-1α plus DCoH. Chinese hamster ovary (CHO) cells were used as the recipients since untransfected cells have no HNF-1α or DCoH background. HNF-1α s able to activate transcription of a fusion gene with three HNF-1α sites directing transcription of chloramphenicol acetyl transferase ("CAT") [(β28)$_{3-cat}$] in the CHO cells. Cotransfection of increasing amounts of the DCoH expression vector along with 5 μg of the HNF-1α expression vector results in a dose dependent increase in the HNF-1α dependent CAT activity up to five times the CAT activity observed with the addition of 5 μg of the HNF-1α expression vector alone. DCoH is similarly able to augment the transcriptional activity of HNF-1α via a promoter composed of a fragment of the natural α fibrinogen promoter (αFg-CAT). Since this promoter contains a single HNF-1 binding site in the context of binding sites for other factors it was concluded that the effect of DCoH cannot be attributed to the artificial nature of the three tandemly linked HNF-1α binding sites. Likewise, the DCoH expression vector, or the expression vector by itself, are not able to induce reporter gene activity, indicating that the measured CAT activity is indeed HNF-1 dependent.

Using 5 μg of the HNF-1α expression vector, substantial HNF-1-dependent CAT activity (15% conversion in a 2 h assay) was observed even in the absence of DCoH. When the HNF-1α expression vector was used at levels of 10 ng, which does not exhibit substantial activity, a reproducible 200-fold induction of HNF-1-dependent CAT activity was observed with coexpression of DCoH.

Testing with other transcriptional factors, such as GHF-1/Pit-1 (Bodner et al., 1988; Ingraham et al., 1988) with DCoH did not enhance the amount of GHF-1-dependent CAT activity. Upon transfection of DCoH with the glucocorticoid receptor, enhancement of the ability of the glucocorticoid receptor to activate transcription of the MMTV promoter was observed. The enhancement was about 1.5 fold.

To investigate the mechanism by which DCoH enhances the transcriptional activity of HNF-1α, the full DCoH sequence was linked to the amino end of the 147 amino acids which contain the DNA binding and dimerization domains of GAL4 to provide a fusion protein. The DCoH-GAL4 protein was not able to activate transcription of a reporter construct driven by five tandemly arranged GAL4 binding sites. These results would suggest that DCoH cannot provide a transcriptional activation domain for the GAL4 DNA binding site.

The ribonuclease protection assay was used to test for the presence of DCoH message in adult murine organs. The message for DCoH is most abundant in liver and kidney, is present in lower levels in intestine and stomach, and at still lower levels in lung, ovary and brain. A labelled antisense riboprobe made from the M1 insert detects DCoH message at low levels in rat heart. The brain and the heart are the only tissues tested that contain detectable DCoH message but do not contain the message for either HNF-1α or -1β and none of the tissues which contain message for HNF-1α or -1β lack the message for DCoH. Furthermore, the expression of DCoH message is highest in the liver and kidney, which tissues contain the highest amount of HNF-1α protein in Vivo (Baumheuter et al., 1990).

The message for DCoH is abundant in well differentiated hepatocyte cell lines, such as the murine HepalA and rat Fao cells which express most of the hepatocyte-enriched gene products, and which express predominantly, or exclusively, HNF-1α binding activity (Mendel et al., 1991). The message for DCoH is also expressed, albeit at lower levels in the C2 de-differentiated hepatocyte cell line, isolated from the Fao parent cell line (Deschatrette et al., 1974; Deschatrette et al., 1980) and the FF5 somatic hybrids generated by fusing Fao cells with fibroblasts (Killary et al., 1984). Both the C2 and FF5-1 cell lines only express a limited number of hepatocyte specific gene products and express HNF-1β instead of HNF-1α (Mendel et al., 1991; Rey-Campos et al., 1991; Baumhueter et al., 1988; Cereghini et al., 1988; DeSimone et al., 1991). An antibody to DCoH was produced by injection of recombinant protein into mice. The antibody was then used to examine the pattern of expression of the HNF-1 protein by virtue of the fact that the antibody produced a supershifted gel mobility shift complex, with HNF-1α or HNF-1β, DCoH and the DNA. DCoH protein could be detected in the kidney, liver, lung and several cell lines using this approach. These results indicate the DCoH participates in the formation of functional multimeric transcriptional complexes in vivo.

It is evident from the above results, that transcription can be regulated by controlling a cofactor which binds to transcription factors. Having the amino acid sequence and the nucleic acid sequence allows for the identification of other transcriptional factors which have homology to the subject factor. By identifying these factors, genetic diseases associated with mutant alleles may be subject to modification or treatment. Furthermore, where genes associated with various diseases, are dependent upon the expression of cofactors for transcription factors, various nucleic acids or peptides may be employed for therapeutic purposes to inhibit expression of the genes. Antibodies and DNA probes may be used to follow the course of expression of the DCoH and related genes for investigating cellular responses to stimuli, secondary message pathways, and the like.

The subject invention extends the insights into the nature of transcription. This insight can be used widely in developing new approaches to diagnosis and therapy. In addition, by using cofactor expression or inhibition of cofactor expression, one can modulate the production of a wide variety of products which are produced in culture.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

REFERENCES

Abbott, C., Piaggio, G., Ammendola, R., Solomon, E., Povey, S., Gounari, F., De Simone, V., and Cortese, R.

(1990). Mapping of the gene TCF2 coding for the transcription factor LFB3 to human chromosome 17 by polymerase chain reaction. Genomics 8, 165–167.

Alwine, J. C., Kemp, D. J., and Stark, G. R. (1977). Method for detection of specific RNAs in agarose gels by transfer to diazobenzyloxymethyl-paper and hybridization with DNA probes. Proc. Natl. Acad. Sci. USA 74, 5350–5354.

Bach, I., Galcheva-Gargova, Z., Mattei, M.-G., Simon-Chazottes, D., Guenet, J.-L., Cereghini, S., and Yaniv, M. (1990). Cloning of human hepatic nuclear factor 1 (HNF1) and chromosomal localization of its gene in man and mouse. Genomics 8,155–164.

Baumhueter, S., Courtois, G., and Crabtree, G. R. (1988). A variant nuclear protein in dedifferentiated hepatoma cells binds to the same functional sequences in the b fibrinogen gene promoter as HNF-1 . EMBO J. 7, 2485–2493.

Baumhueter, S., Mendel, D. B., Conley, P. B., Kuo, C. J., Turk, C., Graves, M. K., Edwards, C. A., Courtois, G., and Crabtree, G. R. (1990). HNF-1 shares three sequence motifs with the POU domain proteins and is identical to LF-B1 and APF. Genes Dev. 4, 372–379.

Berger, S. L., Cress, W. D., Cress, A., Triezenberg, S. J., and Guarente, L. (1990). Selective inhibition of activated but not basal transcription by the acidic activation domain of VP16: Evidence for transcriptional adaptors. Cell 61, 1199–1208.

Bodner, M., Castrillo, J.-L., Theill, L. E., Deerinck, T., Ellisman, M., and Karin, M. (1988). The pituitary-specific transcription factor GHF-1 s a homeobox-containing protein. Cell 55, 505–518.

Brennan, R. G. and Matthews, B. W. (1989). The helix-turn-helix DNA binding motif. J. Biol. Chem. 264, 1903–1906.

Carey, M., Kakidani, H., Leatherwood, J., Mostashari, F., and Ptashne, M. (1989). An amino-terminal fragment of GAL4 binds DNA as a dimer. J. Mol. Biol. 209, 423–432.

Cereghini, S., Blumenfeld, M., and Yaniv, M. (1988). A liver-specific factor essential for albumin transcription differs between differentiated and dedifferentiated rat hepatoma cells. Genes Dev 8, 957–974.

Cereghini, S., Yaniv, M., and Cortese, R. (1990). Hepatocyte dedifferentiation and extinction is accompanied by a block in the synthesis of mRNA coding for the transcription factor HNF1/LFB1. EMBO J. 9 (7), 2257–2263.

Chasman, D. I., Leatherwood, J., Carey, M., Ptashne, M., and Kornberg, R. D. (1989). Activation of yeast polymerase II transcription by Herpesvirus VP16 and GAL4 derivatives in vitro. Mol. Cell. Biol. 9, 4746–4749.

Chirgwin, J. M., Przybyla, A. E., MacDonald, R. J., and Rutter, W. J. (1979). Isolation of biologically active ribonucleic acid from sources enriched in ribonuclease. Biochemistry 18, 5294–5299.

Chouard, T., Blumenfeld, M., Bach, I., Vandekerckhove, J., Cereghini, S., and Yaniv, M. (1990). A distal dimerization domain is essential for DNA-binding by the atypical HNF1 homeodomain. Nucleic Acids Res. 18, 5853–5863.

Courtois, G., Baumhueter, S., and Crabtree, G. R. (1988). Purified hepatocyte nuclear factor 1 interacts with a family of hepatocyte-specific promoters. Proc. Natl. Acad. Sci. USA 85, 7937–7941.

Courtois, G., Morgan, J. G., Campbell, L. A., Fourel, G., and Crabtree, G. R. (1987). Interaction of a liver-specific nuclear factor with the fibrinogen and alpha1-antitrypsin promoters. Science 238, 688–692.

Danielsen, M., Northrop, J. P., and Ringold, G. M. (1986). The mouse glucocorticoid receptor: mapping of functional domains by cloning, sequencing and expression of wild-type and mutant proteins. EMBO J. 5, 2513–2522.

De Simone, V., De Magistris, L., Lazzaro, D., Gerstner, J., Monaci, P., Nicosia, A., and Cortese, R. (1991). LFB3, a heterodimer-forming homeoprotein of the LFB1 family, is expressed in specialized epithelia. EMBO J. 10, 1435–1443.

Deschatrette, J., Moore, E. E., Dubois, M., and Weiss, M. (1980). Dedifferentiated variants of a rat hepatoma: reversion analysis. Cell 19, 1043–1051.

Deschatrette, J. and Weiss, M. C. (1974). Characterization of differentiated and dedifferentiated clones of a rat hepatoma. Biochimie 56, 1603–1611.

Evans, R. M. (1988). The steroid and thyroid hormone receptor superfamily. Science 240, 889–895.

Flanagan, P. M., Kelleher III, R. J., Sayre, M. H., Tschochner, H., and Kornberg, R. D. (1991). A mediator required for activation of RNA polymerase II transcription in vitro. Nature 350, 436–438.

Fowlkes, D. M., Mullis, N. T., Comeau, C. M., and Crabtree, G. R. (1984). Potential basis for regulation of the coordinately expressed fibrinogen genes: homology in the 5= flanking regions. Proc. Natl. Acad. Sci. USA 81, 2313–2316.

Frain, M., Swart, G., Monaci, P., Nicosia, A., Stmpfli, S., Frank, R., and Cortese, R. (1989). The liver-specific transcription factor LF-B1 contains a highly diverged homeobox DNA binding domain. Cell 59, 145–157.

Fried, M. G. and Crothers, D. M. (1981). Equilibria and kinetics of lac repressor-operator interactions by polyacrylamide gel electrophoresis. Nuc. Acid. Res. 9, 6505–6526.

Friedman, J. M., Babiss, L. E., Weiss, M., and Darnell JE, J.r. (1987). Hepatoma variants (C2) are defective for transcriptional and post-transcriptional actions from both endogenous and viral genomes. EMBO. J. 6, 1727–1731.

Gehring, W. J. (1987). Homeo boxes in the study of development. Science 236, 1245–1252.

Gentz, R., Rauscher, F. J.,III, Abate, C., and Curran, T. (1989). Parallel association of Fos and Jun leucine zippers juxtaposes DNA binding domains. Science 243, 1695–1699.

Gorman, C. M., Moffat, L. F., and Howard, B. H. (1982). Recombinant genomes which express choramphenicol acetyltransferase in mammalian cells. Mol Cell Biol 2, 1044–1050.

Herr, W., Sturm, R. A., Clerc, R. G., Corcoran, L. M., Baltimore, D., Sharp, P. A., Ingraham, H. A., Rosenfeld, M. G., Finney, M., Ruvkun, G., and Horvitz, H. R. (1988). The POU domain: A large conserved region in the mammalian pit-1, oct-1, oct-2, and Caenorhabditis elegans unc- 86 gene products. Genes Dev. 2, 1513–1516.

Herskowitz, I. (1989). A regulatory hierarchy for cell specialization in yeast. Nature 342, 749–757.

Ho, S. N., Hunt, H. D., Horton, R. M., Pullen, J. K., and Pease, L. R. (1989). Site-directed mutagensis by overlap extension using the polymerase chain reaction. Gene 77, 51–59.

Hogan, B. L. M. and Taylor, A. (1981). Cell interactions modulate embryonal carcinoma cell differentiation into parietal or visceral endoderm. Nature 291, 235–237.

Hope, I. A. and Struhl, K. (1987). GCN4, a eukaryotic transcriptional activator protein, binds as a dimer to target DNA. EMBO. J. 6, 2781–2784.

Horton, R. M., Hunt, H. D., Ho, S. N., Pullen, J. K., and Pease, L. R. (1989). Engineering hybrid genes without the use of restriction enzymes: gene splicing by overlap extension. Gene 77, 61–68.

Ingraham, H. A., Chen, R., Mangalam, H. J., Elsholtz, H. P., Flynn, S. E., Lin, C. R., Simmons, D. M., Swanson, L., and Rosenfeld, M. G. (1988). A tissue-specific transcription factor containing a homeodomain specifies a pituitary phenotype. Cell 55, 519–529.

Ingraham, H. A., Flynn, S. E., Voss, J. W., Albert, V. R., Kapiloff, M. S., Wilson, L., and Rosenfeld, M. G. (1990). The POU-specific domain of Pit-1 s essential for sequence-specific, high affinity DNA binding and DNA-dependent Pit-1-Pit-1 interactions. Cell 61, 1021–1033.

Jarvis, E. E., Hagan, D.C., and Sprague, G. F. (1988). Identification of a DNA segment that is necessary and sufficient for a-specific gene control in Saccharomyces cerevisiae. Mol. Cell. Biol. 8, 309–320.

Johnson, W. A. and Hirsh, J. (1990). Binding of a Drosophila POU-domain protein to a sequence element regulating gene expression in specific dopaminergic neurons. Nature 343, 467–470.

Jones, Nic. (1990). Transcriptional regulation by dimerization: Two sides to an incestuous relationship. Cell 61, 9–11.

Kadonaga, J. T. and Tjian, R. (1986). Affinity purification of sequence-specific DNA binding proteins. Proc. Natl. Acad. Sci USA 83, 5889–5893.

Keegan, L., Gill, G., and Ptashne, M. (1986). Separation of DNA binding from the transcription-activating function of a eukaryotic regulatory protein. Science 231, 699–704.

Keleher, C. A., Goutte, C., and Johnson, A. D. (1988). The yeast cell-type-specific repressor alpha 2 acts cooperatively with a non-cell-type-specific protein. Cell 53, 927–936.

Kelleher, R. J.,III, Flanagan, P. M., and Kornberg, R. D. (1990). A novel mediator between activator proteins and the RNA polymerase II transcription apparatus. Cell 61, 1209–1215.

Killary, A. M. and Fournier, R. E. (1984). A genetic analysis of extinction: trans-dominant loci regulate expression of liver-specific traits in hepatoma hybrid cells. Cell 38, 523–534.

Kozak, M. (1986). Point mutations define a sequence flanking the AUG initiator codon that modulates translation by eukaryotic ribosomes. Cell 44, 283–292.

Kuo, C. J., Conley, P. B., Hsieh, C., Franke, U., and Crabtree, G. R. (1990). Molecular cloning, functional expression and chromosomal localization of murine HNF-1. Proc. Natl. Acad. Sci. USA 87, 9838–9842.

Kuo, C. J., Mendel, D. B., Hansen, L. P., and Crabtree, G. R. (1991). Independent regulation of HNF-1α la and HNF-1b by retinoic acid in F9 teratocarcinoma cells. EMBO J. 10, 2231–2236.

Laemmli, U. K. (1970). Cleavage of structural proteins during the assembly of the head of bacteriophage T4. Nature 27, 680–685.

Landschulz, W. H., Johnson, P. F., and McKnight, S. L. (1988). The leucine zipper: A hypothetical structure common to a new class of DNA binding proteins. Science 240, 1759–1764.

Landschulz, W. H., Johnson, P. F., and McKnight, S. L. (1989). The DNA binding domain of the rat liver nuclear protein C/EBP is bipartite. Science 243, 1681–1688.

Lefevre, C., Imagawa, M., Dana, S., Grindlay, J., Bodner, M., and Karin, M. (1987). Tissue-specific expression of the human growth hormone gene is conferred in part by the binding of a specific trans-acting factor. EMBO. J. 6, 971–981.

Lewin, B. (1990). Commitment and activation at Pol II promoters: A tail of protein-protein interactions. Cell 61, 1161–1164.

Lillie, J. W. and Green, M. R. (1989). Transcription activation by the adenovirus Ela protein. Nature 338, 39–44.

Lin, Y-S. and Green, M. R. (1991). Mechanism of action of an acidic transcriptional activator in vitro. Cell 64, 971–981.

Ma, J. and Ptashne, M. (1987). Deletion analysis of GAL4 defines two transcriptional activating segments. Cell 48, 847–853.

Maire, P., Wuarin, J., and Schibler, U. (1989). The role of cis-acting promoter elements in tissue-specific albumin gene expression. Science 244, 343–346.

Mendel, D. B. and Crabtree, G. R. (1991). HNF-1, a member of a novel class of dimerizing homeodomain proteins. J. Biol. Chem. 266, 677–680.

Mendel, D. B. , Hansen, L. P., Graves, M. K. , Conley, P. B., and Crabtree, G. R. (1991). HNF-1a and HNF-1b (vHNF-1) share dimerization and homeo domains, but not activation domains, and form heterodimers in vitro. Genes Dev. 5, 1042–1056.

Nicosia, A., Monaci, P., Tomei, L., De Francesco, R., Nuzzo, M., Stunnenberg, H., and Cortese, R. (1990). A myosin-like dimerization helix and an extra-large homeodomain are essential elements of the tripartite DNA binding structure of LFB1. Cell 61, 1225–1236.

Northrop, J. P., Gametchu, B., Harrison, R. W., and Ringold, G. M. (1985). Characterization of wild type and mutant glucocorticoid receptors from rat hepatoma and mouse lymphoma cells. J. Biol. Chem. 260, 6398–6403.

Passmore, S., Elble, R., and Tye, B. ( 1989 ). A protein involved in minichromosome maintenance in yeast binds a transcriptional enhancer conserved in eukaryotes. Genes Dev. 3, 921–935.

Pugh, B. F. and Tjian, R. (1990) . Mechanism of transcriptional activation by Spl: Evidence for coactivators. Cell 61, 1187–1197.

Rey-Campos, J., Chouard, T., Yaniv, M., and Cereghini, S. ( 1991 ) . vHNF1 s a homeoprotein that activates transcription and forms heterodimers with HNF1. EMBO J. 10, 1445–1457.

Rosenfeld, P. J. and Kelly, T. J. (1986). Purification of Nuclear factor 1 by DNA Recognition site affinity chromatography. J. Biol. Chem. 261, 1398–1408.

Sadowski, I., Ma, J., Triezenberg, S., and Ptashne, M. (1988). GAL4-VP16 is an unusually potent transcriptional activator. Nature 335, 563–564.

Scott, M. P., Tamkun, J. W., and Hartzell, G. W. (1990). The Structure and Function of the Homeodomain. Biochem. Biophys. Acta. 989, 25–48.

Scott, R. W., Vogt, T. F., Croke, M. E., and Tilghman, S.M. (1984). Tissue-specific activation of a cloned alpha-fetoprotein gene during differentiation of a transfected embryonal carcinoma cell line. Nature 310 (5978), 562–567.

Stern, S., Tanaka, M., and Herr, W. (1989). The Oct-1 homoeodomain directs formation of a multiprotein-DNA complex with the HSV transactivator VP16. Nature 341, 624–630.

Strauss, F. and Varshavsky, A. (1984). A protein binds to a satellite DNA repeat at three specific site s that would be brought into proximity by DNA folding in the nucleosome Cell 37, 889–901.

Stringer, K. F., Ingles, J., and Greenblatt, J. (1990). Direct and selective binding of an acidic transcriptional activation domain to the TATA-box factor TFIID. Nature 345, 783–786.

Theill, L. E., Castrillo, J. -L., Wu, D., and Karin, M. (1989). Dissection of functional domains of the pituitary-specific transcription factor GHF-1. Nature 342, 945–948.

Thomas, P. S. (1980). Hybridization of denatured RNA and small DNA fragments transferred to nitrocellulose. Proc. Natl. Acad. Sci. USA 77, 5201–5205.

Treacy, M. N., He, X., and Rosenfeld, M. G. (1991). I-POU: A POU-domain protein that inhibits neuron-specific gene activation. Nature 350, 577–584.

Triezenberg, S. J., Kingsbury, R. C., and McKnight, S. L. (1988). Functional dissection of VP16, the trans-activator of herpes simplex virus immediate early gene expression. Genes Dev. 2, 718–729.

Turner, R. and Tjian, R. (1989). Leucine repeats and an adjacent DNA binding domain mediate the formation of functional cFos-cJun heterodimers. Science 243, 1689–1694.

Voss, J. W., Wilson, L., and Rosenfeld, M. G. (1991). POU-domain proteins Pit-1 and Oct-1 interact to form a heteromeric complex and can cooperate to induce expression of the prolactin promoter. Genes Dev 5, 1309–1320.

Young, P. R. and Tilghman, S. M. (1984). Induction of alpha-fetoprotein synthesis in differentiating F9 teratocarcinoma cells is accompanied by a genome-wide loss of DNA methylation. Mol. Cell Biol. 4, 898–907.

de Wet, J. R., Wood, K. V., DeLuca, M., Helinski, D. R., and Subramani, S. (1987). The firefly luciferase gene: structure and expression in mammalian cells. Mol. Cell. Biol. 7, 725–737.

What is claimed is:

1. A purified mammalian nucleic acid sequence, having other than the naturally occurring wild-type flanking sequence when said nucleic acid sequence is DNA, encoding a transcription cofactor, wherein said transcription cofactor is characterized by:

having a molecular weight of about 11 kd;

having a domain of from about 20 to 50 amino acids, which is lipophilic in having a plurality of hydrophobic aliphatic and aromatic amino acids;

existing as dimers in a nuclear extract;

capable of enhancing dimerization of transcription factors; and not having a specific binding affinity for the DNA sequence to which said transcription factors bind; and fragments thereof of at least about 24 consecutive nucleotides.

2. The nucleic acid sequence according to claim 1, wherein said cofactor binds to at least one of HNF-1α dimer and HNF-1β and a heterodimer of HNF-1α and HNF-1β.

3. The nucleic acid sequence according to claim 1, wherein said sequence is DNA.

4. The nucleic acid sequence according to claim 1, wherein said nucleic acid is from a human cell.

5. A vector comprising a marker and a nucleic acid sequence according to claim 1, wherein said nucleic acid sequence is DNA.

6. A host cell comprising a vector, said vector comprising a marker and a nucleic acid sequence according to claim 1, wherein said nucleic acid sequence is DNA.

7. A nucleic acid sequence comprising a nucleic acid sequence of a transcription factor according to claim 1, joined to a second nucleic acid sequence not naturally joined to said transcription factor nucleic acid sequence.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 949 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
GAATTCCGGT  TTTATAGCAA  GGACATTACA  TTTTCAGGTA  CCTAAAGTCA  AAATTCAACA      60
CACTGATATA  AAACTTCTAT  TTAAACCAAT  AGGGTTCTGT  TATGATATTG  ATCTGTTCAC     120
AGTAACATTT  ACAAAAAGAG  GCAGAGGCAG  GGGGATCTCT  GCCCCGCCCC  CGCGGTGGCC     180
TGCTGCCTGC  CAGCCGCTCT  CCCTCGCTGA  CGCCACCTGC  TTCCCGCACT  GGACATGGCT     240
GGCAAGGCAC  ACAGGCTGAG  TGCTGAGGAA  CGGGACCAGC  TGCTGCCAAA  CCTGCGGGCT     300
GTGGGGTGGA  ATGAACTGGA  AGGCCGAGAT  GCCATCTTCA  AACAGTTCCA  TTTTAAAGAC     360
TTCAACAGGG  CTTTTGGCTT  CATGACAAGA  GTCGCCCTGC  AGGCTGAAAA  GCTGGACCAC     420
CATCCCGAGT  GGTTTAACGT  GTACAACAAG  GTCCATATCA  CCTTGAGCAC  CACGAATGT     480
GCCGGTCTTT  CTGAACGGGA  TATAAACCTG  GCCAGCTTCA  TCGAACAAGT  TGCCGTGTCT     540
ATGACATAGA  TCTACCCTGC  CTCCTATTTC  CTTAGGGGAA  AGGAGAAGGA  GTGACTGGAG     600
GAGGAACCCA  GGGAGGGAAC  CAAGGAGGCT  GGCCCTTGCT  CCCTGACTCT  TGCGGTGACC     660
ACCATCTCCG  TCAGGAGGGG  TATGAGTCCC  TCCCTGTGCA  GAACGATGCC  CATGTTCCTG     720
GTGCCAGCCT  CCTCACTGGG  CTCTGCCATG  TTTATAATTT  GAATAAGCTC  TCCCATTTTC     780
TATAGAGTTC  CTAGCCTCAG  TTGTGTCCCA  GGCTGCCTCT  TGCTCCTTGT  CTACCGGTTC     840
TAGTTAATTT  TCCAAGTAGC  TGTGATAAAG  CATGACAGAA  AGTCCAATTC  AGACCCTACT     900
AAAACAAACC  CCAATATATT  ATGGAAACAG  TGCTTTTATG  CCGGAATTC                  949
```

( 2 ) INFORMATION FOR SEQ ID NO:2:

( i ) SEQUENCE CHARACTERISTICS:
( A ) LENGTH: 778 base pairs ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
| GCTGGCAAAG | CACACAGGCT | GAGCGCTGAG | GAGAGGGACC | AGCTACTGCC | AAACCTGAGG | 60 |
| GCTGTGGGGT | GGAATGAGCT | GGAAGGCCGT | GATGCCATCT | TCAAGCAGTT | TCATTTCAAA | 120 |
| GACTTCAACA | GGGCCTTTGG | GTTCATGACA | AGAGTGGCCC | TGCAGGCTGA | GAAACTGGAC | 180 |
| CACCATCCTG | AATGGTTTAA | CGTGTACAAC | AAGGTCCACA | TCACGCTGAG | CACCCATGAG | 240 |
| TGTGCCGGCC | TTTCAGAACG | GGACATAAAC | CTGGCCAGCT | TCATCGAACA | AGTAGCCGTG | 300 |
| TCCATGACAT | AGACCCTGCC | CTTCCTTCTT | TGAATTCTTC | CGGGGGAAAG | GGTGACTGAA | 360 |
| CTGGGAGTCC | AGGGAGGGAG | CTGAGGAGCC | CTTACCCTCC | CACCACTCCC | CTCCCAAGAC | 420 |
| CCAGCCGCCG | CCGTTGAGGG | CTGAGTCCTT | GCTGTGGGAT | GTGCCAGTGT | CCCCACCAAC | 480 |
| ACCAGGAATT | TAGACCTTTT | CCCTGCACCA | CTCTCTTCAT | CCTGGGGGC | TCTGTTACAC | 540 |
| TAATGTAATA | AACTCTCCCC | TTTTCTTTGC | AACTTCCCAG | CAACAATAAT | GATTTCTTG | 600 |
| CCAGGCCGTC | TCTTGCTCCC | TAATTCATTT | CCCAGGAAGC | TGTGATACAG | GGTGAAATAA | 660 |
| AGTCTTGTCT | TAGAAACCAG | GACCCTAAAC | CCCACACTAT | GTAATAGAAA | CACATGTGTT | 720 |
| TTTATGTCTC | AAATAAAACT | ATTATATCAC | TTGGTAAAAA | AAAAAAAAA | AAGAATTC | 778 |

( 2 ) INFORMATION FOR SEQ ID NO:3:

( i ) SEQUENCE CHARACTERISTICS:
            ( A ) LENGTH: 739 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| CACAGGCTGA | GCGCCGAGGA | GAGGACCAGC | TACTGCCAAA | CCTGAGGGCT | GTGGGGTGGA | 60 |
| ATGAGTAGAA | GGCCGAGATG | CTATCTTCAA | GCAGTTCCAT | TTTAAAGACT | TCAACAGGGC | 120 |
| TTTTGGCTTC | ATGACAAGAG | TAGCCCTGCA | GGCTGAAAAG | CTGGACCACC | ATCCCGAGTG | 180 |
| GTTTAACGTG | TACAACAAGG | TCCATATCAC | CTTGAGCACC | CATGAATGTG | CCGGTCTTTG | 240 |
| TGAACGGGAT | ATAAACCTGG | CCAGCTTCAT | CGAACAAGTC | GCCGTGTCTA | TGACATAGAT | 300 |
| CTACCCTGAC | TCTTATTTGC | TTGGGGGAAG | GAGTGACTGG | AGGAGGAACC | TAGGAAGGGA | 360 |
| ACCAAGGAGG | CTGGCCCTTG | CTCCCTGACT | CTTTCAGTGA | CCACCACCTC | CCTATGCAGA | 420 |
| AGGGATGTCA | ATGTCAACAG | CAGGGACTGA | GACCTTTCTC | TGTGCCACTC | TCCTCACTGG | 480 |
| GGCTCTGCCA | TGTTACACTA | ATTTGAATAA | GCTCTCCCTT | TTTCTGTAGA | GTTCCCAGCC | 540 |
| TCAGTAATGT | TCCAGGCTGG | CTTCTTGTTC | CTTTTCTACC | CTTTCTAGTT | CATTTTCCAA | 600 |
| GGTAGCTGTG | ATAAAGCATG | ACATAAAAGC | CCAATTCAGA | TCCTACTAAT | AAAACAAGCT | 660 |
| CCAATGTATT | ATGGAAACAT | GTGCTTTTAC | GCCTCCAATA | AACTATGTT | ATCGATGAAA | 720 |
| AAAAAAAAA | AAGGAATTC | | | | | 739 |

( 2 ) INFORMATION FOR SEQ ID NO:4:

( i ) SEQUENCE CHARACTERISTICS:
            ( A ) LENGTH: 104 amino acids
            ( B ) TYPE: amino acid
            ( C ) STRANDEDNESS: single ( D ) TOPOLOGY: linear ( i i ) MOLECULE TYPE: protein ( x i ) SEQUENCE DESCRIPTION: SEQ ID NO:4:

| Met | Ala | Gly | Lys | Ala | His | Arg | Leu | Ser | Ala | Glu | Glu | Arg | Asp | Gln | Leu |
| 1 | | | | 5 | | | | | 10 | | | | | 15 | |

| Leu | Pro | Asn | Leu | Arg | Ala | Val | Gly | Trp | Asn | Glu | Leu | Glu | Gly | Arg | Asp |
| | | | 20 | | | | | 25 | | | | | 30 | | |

| Ala | Ile | Phe | Lys | Gln | Phe | His | Phe | Lys | Asp | Phe | Asn | Arg | Ala | Phe | Gly |
| | | 35 | | | | | 40 | | | | | 45 | | | |

| Phe | Met | Thr | Arg | Val | Ala | Leu | Gln | Ala | Glu | Lys | Leu | Asp | His | His | Pro |
| | 50 | | | | | 55 | | | | | 60 | | | | |

| Glu | Trp | Phe | Asn | Val | Tyr | Asn | Lys | Val | His | Ile | Thr | Leu | Ser | Thr | His |
| 65 | | | | | 70 | | | | | 75 | | | | | 80 |

| Glu | Cys | Ala | Gly | Leu | Ser | Glu | Arg | Asp | Ile | Asn | Leu | Ala | Ser | Phe | Ile |
| | | | | 85 | | | | | 90 | | | | | 95 | |

| Glu | Gln | Val | Ala | Val | Ser | Met | Thr |
| | | | 100 | | | | |

( 2 ) INFORMATION FOR SEQ ID NO:5:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

GGCGAATTCG ATCGCGATCA TATCTTTCAA GAGA 34

( 2 ) INFORMATION FOR SEQ ID NO:6:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

GGCAAGCTTG ATCGATCAGA TCTTTCTCGA TCGCTCTG 38

( 2 ) INFORMATION FOR SEQ ID NO:7:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

GCCGAATTCG GAGCCATGGG GGAGCCAGG 29

( 2 ) INFORMATION FOR SEQ ID NO:8:

( i ) SEQUENCE CHARACTERISTICS:
( A ) LENGTH: 7 amino acids
( B ) TYPE: amino acid
( C ) STRANDEDNESS: single
( D ) TOPOLOGY: linear (ii) MOLECULE TYPE: peptide (xi) SEQUENCE DESCRIPTION: SEQ ID NO:8:

Met Gly Glu Pro Gly Pro Tyr
1               5

(2) INFORMATION FOR SEQ ID NO:9:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:9:

Ser Lys Glu Ala Leu Ile Gln Ala Arg Gly Ser Glu Asp Asp
1               5                   10

(2) INFORMATION FOR SEQ ID NO:10:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:10:

GTCTATGACA ATGAAGCTAC TGTC     24

(2) INFORMATION FOR SEQ ID NO:11:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:11:

GTAGCTTCAT TGTCATAGAC ACGG     24

(2) INFORMATION FOR SEQ ID NO:12:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:12:

GGCCGAATTC GCACTGGACA TGGCTGGCAA G     31

(2) INFORMATION FOR SEQ ID NO:13:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: cDNA ( x i ) SEQUENCE DESCRIPTION: SEQ ID NO:13:

GGCCGAATTC TACGATACAG TCAACTG 27

( 2 ) INFORMATION FOR SEQ ID NO:14:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Val Ala Val Ser Met Thr Met Lys Leu Leu Ser Ser
1                5                   10